(12) United States Patent
Suzuki et al.

(10) Patent No.: US 6,988,985 B2
(45) Date of Patent: Jan. 24, 2006

(54) TISSUE PIERCING DEVICE FOR AN ENDOSCOPE

(75) Inventors: Takayuki Suzuki, Yokohama (JP); Pankaj P. Pasricha, Houston, TX (US)

(73) Assignee: Olympus Optical Co., Ltd., Tokyo (JP)

( * ) Notice: Subject to any disclaimer, the term of this patent is extended or adjusted under 35 U.S.C. 154(b) by 164 days.

(21) Appl. No.: 10/336,021

(22) Filed: Jan. 3, 2003

(65) Prior Publication Data
US 2003/0130560 A1  Jul. 10, 2003

Related U.S. Application Data

(62) Division of application No. 09/909,980, filed on Jul. 23, 2001, now Pat. No. 6,921,361.

(60) Provisional application No. 60/220,204, filed on Jul. 24, 2000.

(51) Int. Cl.
*A61B 1/018* (2006.01)
*A61B 17/062* (2006.01)

(52) U.S. Cl. .............. 600/104; 600/106; 606/139; 606/144; 606/186

(58) Field of Classification Search ........... 600/104, 600/105, 106, 127; 606/144, 146, 147, 185, 606/186
See application file for complete search history.

(56) References Cited

U.S. PATENT DOCUMENTS

| | | | |
|---|---|---|---|
| 3,643,653 A * | 2/1972 | Takahashi et al. ........ 600/129 |
| 4,493,323 A | 1/1985 | Albright et al. | |
| 5,037,021 A | 8/1991 | Mills et al. | |
| 5,397,326 A | 3/1995 | Mangum | |
| 5,474,543 A | 12/1995 | McKay | |
| 5,741,277 A * | 4/1998 | Gordon et al. ........ 606/144 |
| 5,792,153 A | 8/1998 | Swain et al. | |
| 5,797,927 A * | 8/1998 | Yoon ........ 606/144 |
| 5,814,065 A | 9/1998 | Diaz | |
| 5,860,992 A * | 1/1999 | Daniel et al. ........ 606/145 |
| 5,887,594 A | 3/1999 | LoCicero, III ........ 128/898 |
| 5,895,395 A | 4/1999 | Yeung | |
| 5,984,932 A | 11/1999 | Yoon | |
| 5,993,466 A | 11/1999 | Yoon | |
| 6,071,233 A * | 6/2000 | Ishikawa et al. ........ 600/104 |
| 6,113,609 A | 9/2000 | Adams | |
| 6,179,776 B1 * | 1/2001 | Adams et al. ........ 600/121 |
| 6,352,503 B1 | 3/2002 | Matsui et al. | |
| 6,409,678 B1 * | 6/2002 | Ouchi ........ 600/562 |
| 6,494,888 B1 * | 12/2002 | Laufer et al. ........ 606/153 |
| 6,605,096 B1 | 8/2003 | Ritchart | |
| 6,663,639 B1 | 12/2003 | Laufer et al. | |
| 2002/0111534 A1 | 8/2002 | Suzuki et al. | |
| 2002/0156344 A1 * | 10/2002 | Pasricha et al. ........ 600/113 |
| 2003/0004544 A1 | 1/2003 | Kawashima | |

(Continued)

FOREIGN PATENT DOCUMENTS

JP  2000-033071 A  2/2000

(Continued)

*Primary Examiner*—John P. Leubecker
(74) *Attorney, Agent, or Firm*—Frishauf, Holtz, Goodman & Chick, P.C.

(57) ABSTRACT

A tissue-piercing device is provided for use with a flexible endoscope for suturing or ligating tissues in body cavities. Two flexible sleeves are provided side by side along the endoscope such that a predetermined distance between the sleeves at a distal end of the endoscope is larger than a width of a channel of the endoscope. Two flexible piercing members are slidably provided in the two flexible sleeves, respectively, so as to extend from a proximal end to the distal end of the endoscope. And each of the flexible piercing members includes a needle.

4 Claims, 27 Drawing Sheets

U.S. PATENT DOCUMENTS

| | | |
|---|---|---|
| 2003/0139752 A1* | 7/2003 | Pasricha et al. ............ 606/139 |
| 2003/0171651 A1 | 9/2003 | Page et al. |
| 2003/0199731 A1* | 10/2003 | Silverman et al. ............ 600/29 |
| 2003/0216753 A1* | 11/2003 | Nishtala et al. ............. 606/139 |
| 2004/0138682 A1* | 7/2004 | Onuki et al. ................ 606/144 |

FOREIGN PATENT DOCUMENTS

| | | |
|---|---|---|
| JP | 2000-037348 A | 2/2000 |
| WO | WO 99/22649 | 5/1999 |
| WO | WO 99/22649 | 10/2003 |

* cited by examiner

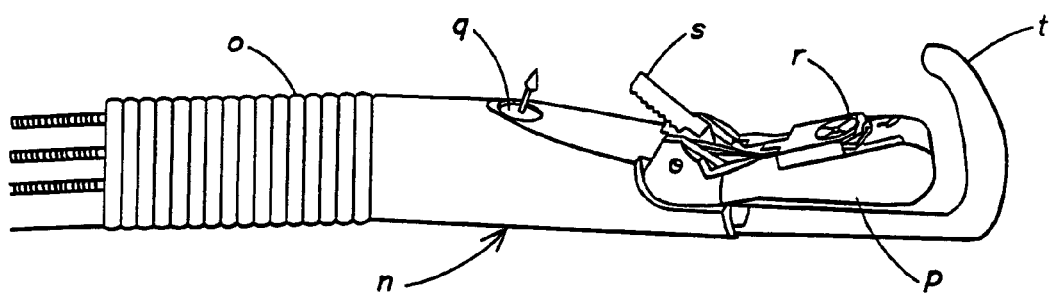
FIG. 42
(Prior Art)
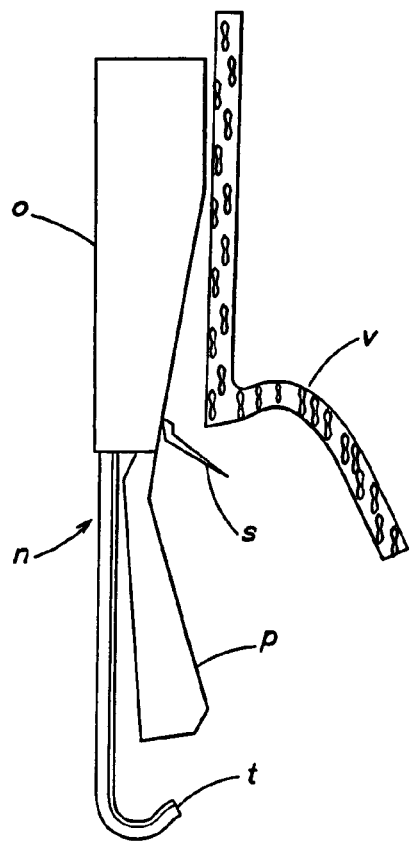 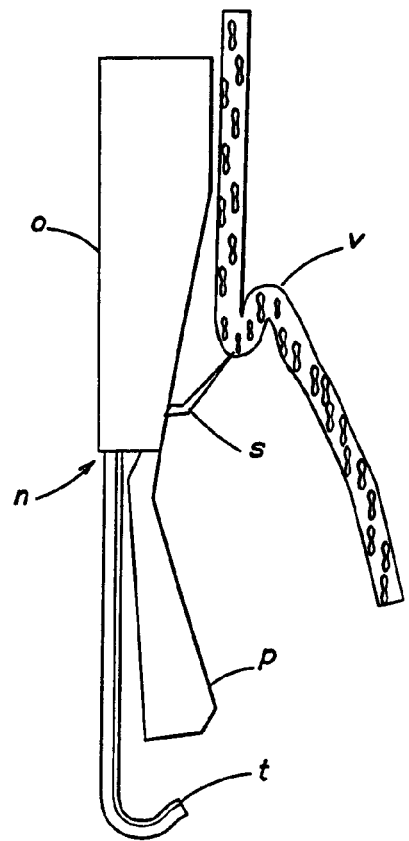
FIG. 43
(Prior Art)
FIG. 44
(Prior Art)

US 6,988,985 B2

TISSUE PIERCING DEVICE FOR AN ENDOSCOPE

CROSS-REFERENCE TO RELATED APPLICATION

This is a division of Ser. No. 09/909,980, filed on Jul. 23, 2001, now U.S. Pat. 6,921,361, which claims the benefit of priority of provisional application Ser. No. 60/220,204, filed on Jul. 24, 2000.

FIELD OF INVENTION

The present invention relates to an apparatus and a method for forming an artificial valve to treat gastroesophageal reflux disease (GERD).

BACKGROUND OF THE INVENTION

The incidence of GERD has increased recently. The main symptoms of GERD are heartburn and mucosal breaks in the esophagus. Although it is a benign disease, GERD is accompanied by serious pain, and often requires treatment. The main cause of GERD is decreased function of the lower esophageal sphincter (LES) at the bottom of the esophagus followed by reflux of acid into the esophagus.

GERD is usually treated by administration of acid secretion controlling agents such as proton-pump inhibitors. Moderate GERD will improve and may be treated completely by medication. If, however, the LES function is damaged seriously or if anatomic problems such as hiatal hernias exist, treatment with medication is less effective, and becomes costly over an extended period of time.

Therefore, cases of serious GERD are often treated surgically. Effective surgical methods—including Nissen fundoplication or the Toupet method—are known and applied widely. With this method, the LES is wrapped by the stomach wall to improve its function.

This method has been proven highly effective. Recently, laparoscopic surgery techniques were used with this method as a less invasive treatment. Because there are many patients, and GERD is a benign disease, these less invasive treatments are desirable.

DESCRIPTION OF THE RELATED ART

FIG. 41 depicts a tool for transoral treatment of GERD, disclosed in U.S. Pat. No. 5,887,594. This instrument a comprises a piercing device e having an elongated portion b, a manipulation section c and a hook portion d; and a securing device i having a connector f, a manipulation section g and a securing mechanism h. The piercing device e is inserted from the mouth to the stomach of a patient, and pulled up to the esophagus, with the hook portion d fixed at the upper stomach thereby forming a fold of tissue (not shown). Then, the securing device i is inserted into the esophagus of the patient, and the securing mechanism h fixes the fold consisting of the upper stomach and the esophagus. When the fold is fixed, the intermediate portion is compressed to inward to form a valve (not shown).

FIGS. 42 to 46 depict another transoral treatment method of GERD, disclosed in International Patent Publication No. WO99/22649. An instrument n has a rotatable fastener head p, which is rotatable at the distal end of a flexible tube o, and the rotatable fastener head p and portion of the flexible tube o that can touch the rotatable fastener head p have a male fastener q and a female fastener r, respectively. The flexible tube o has a rotatable grasper s at the distal end, and an opening for an endoscope t to be inserted throughout the flexible tube o. First, the flexible tube o is inserted from the mouth to the stomach of the patient. The rotatable grasper s is drawn into contact with a junction v between the stomach and the esophagus. The rotatable grasper s is operated to hold the junction v. Next, the flexible tube o is advanced downward to suspend the junction v. The rotatable fastener head p is operated to penetrate the junction v with the male fastener q to engage with the female fastener r. Thus, the junction v and the middle part are compressed to be protruded inward to form a protrusion x.

In the composition disclosed in U.S. Pat. No. 5,887,594, the hook portion d of the piercing device e needs to be fixed to the stomach and pulled. The gastric wall, however, is thicker than the esophagus, and is divided into three regions: the inner mucous membrane; the middle proper muscularis; and the outer serous membrane. In particular, a space between the mucous membrane and the proper muscularis has high movability. To form a protrusion into a valve, tissue including the proper muscularis should be compressed and lifted up. The hook portion d only takes the mucous membrane and cannot include the proper muscularis below it. Thus, the valve formed in this application is not large and thick enough to prevent reflux satisfactorily.

In the apparatus disclosed in International Patent Publication WO99/22649, the rotatable grapser s is integral to the flexible tube o, which makes it difficult to touch the target tissue. The field of view of the endoscope t is blocked by the rotatable fastener head p, which makes difficult for the rotatable grasper s to hold and suspend the junction v between the stomach and the esophagus. Because the position between the rotatable grasper s, the male fastener q, and the female fastener r is fixed, the size of a protrusion x is limited. It is desirable, however, to form a protrusion of varying size depending on the degree of severity of GERD. The difficulty of passing food has already been reported as a complication of artificial cardia in Nissen fondoplication, and is likely to happen with an excessively large protrusion x. Even much a smaller protrusion x is effective for the treatment of the moderate GERD. With this apparatus, treatment is not flexible enough to allow a small protrusion to facilitate food flow in the case of moderate GERD.

SUMMARY OF THE INVENTION

The first object of the present invention is to provide the apparatus and method for forming a valve including the proper muscularis below the mucous membrane to prevent gastroesophageal reflux effectively.

The second object of the present invention is to provide the apparatus and method for holding and suspending the junction between the stomach and the esophagus using a holding device extending out of the distal end of an endoscope to improve the ease of the operation for forming the protrusion.

The third object of the present invention is to provide the apparatus and method for forming a valve of varying size by using a separate holding device and a needle to achieve the flexible treatment method, which may be modified due to the degree of GERD severity.

According to the present invention, an apparatus for forming an artificial valve to treat gastroesophageal reflux disease comprising a first endoscope to be inserted from the mouth into a body cavity; a holding device extending out of the distal end of the first endoscope and holding a point of a digestive wall where the artificial valve is formed; a first needle disposed the oral side of the point, retractable along the first endoscope and including a sharp end for penetrating from the oral side of the point to the anal side of the point; a suture passing through following the first needle; and a suture retaining device having a grasping section for grasping the suture after it has passed through the digestive wall.

According to another aspect of the present invention, a treatment method for forming an artificial valve to treat gastroesophageal reflux disease comprises the following steps. Inserting an endoscope from the mouth substantially adjacent to a point of a digestive wall where the artificial vale is to be formed. Holding a point with a holding device extending out of the distal end of the endoscope. Pulling down the point held by holding device. Penetrating the digestive wall from the oral side of the point to the anal side of the point by a needle positioned along the endoscope. Passing a suture through following the needle. Shortening the digestive wall with the suture to form the artificial valve. Fixing the end of the suture to maintain the artificial valve.

BRIEF DESCRIPTION OF THE DRAWINGS

FIGS. 42 to 46 depict various figures from PCT Application WO99/22649.

DETAILED DESCRIPTION

Figure 1:
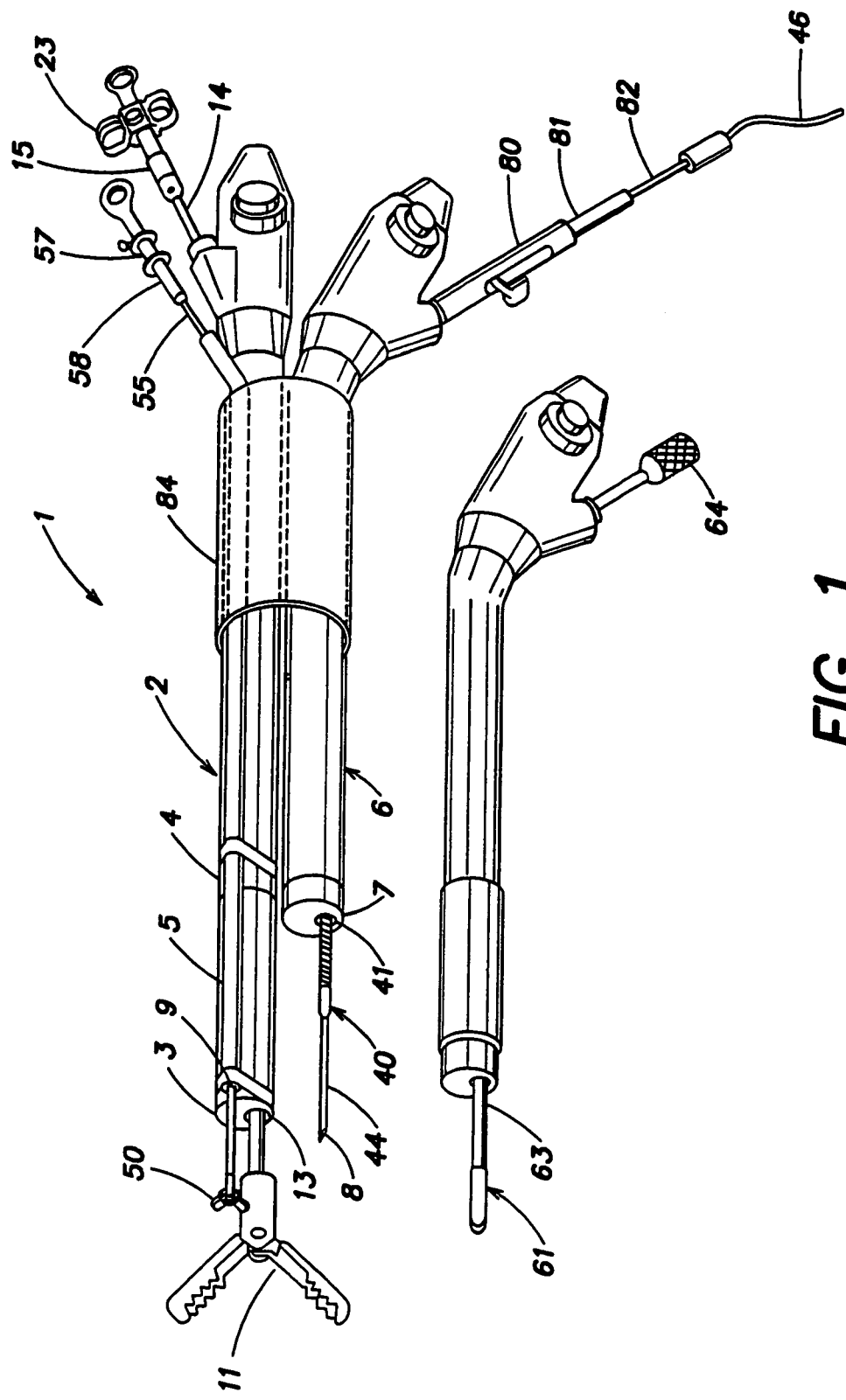
FIG. 1 depicts an arrangement of the first embodiment of the present invention including a first endoscope and a second endoscope.
Figure 2:
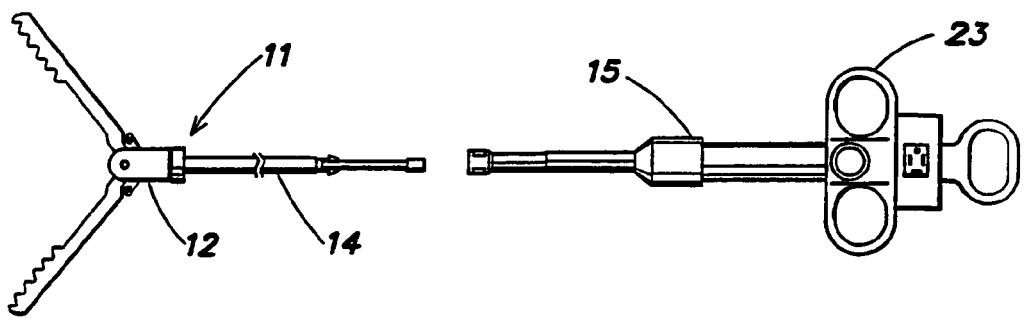
FIG. 2 depicts a holding device of the first embodiment.
Figure 3:
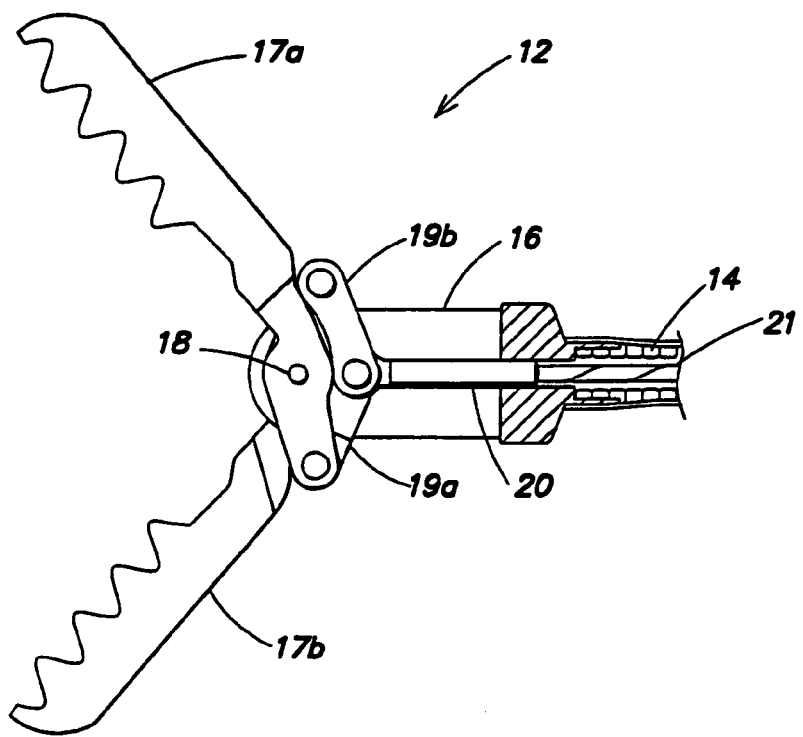
FIG. 3 depicts a detail view of the distal end of the holding device of the first embodiment.
Figure 4:
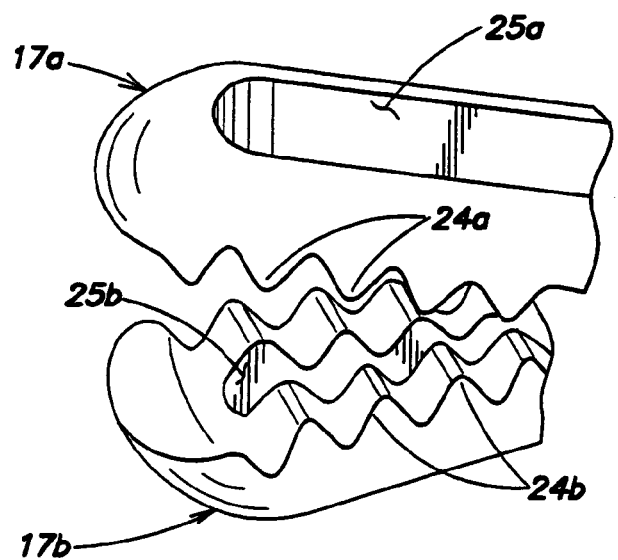
FIG. 4 depicts a detail view of a pair of jaws of the holding device of the first embodiment.
Figure 6:
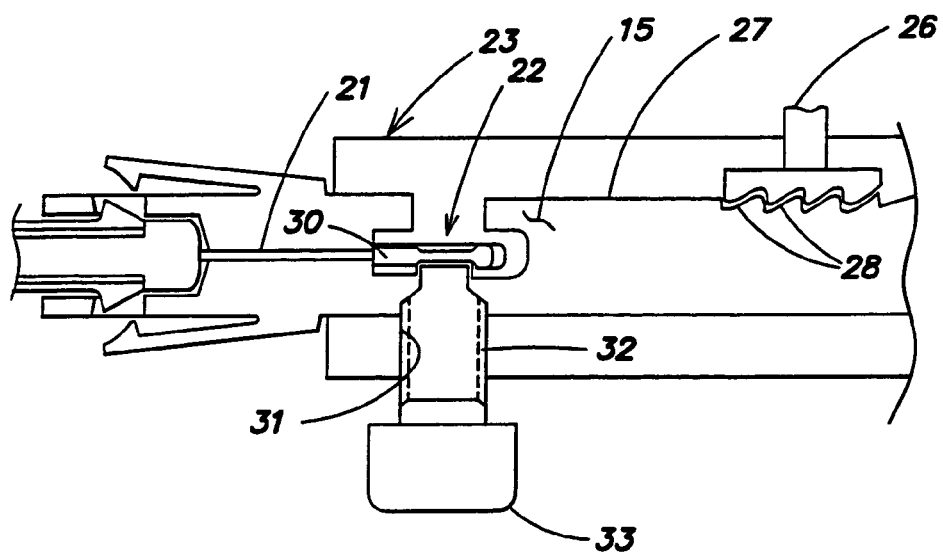
FIG. 6 depicts a cross-section of the connection depicted in FIG. 5.
Figure 5:
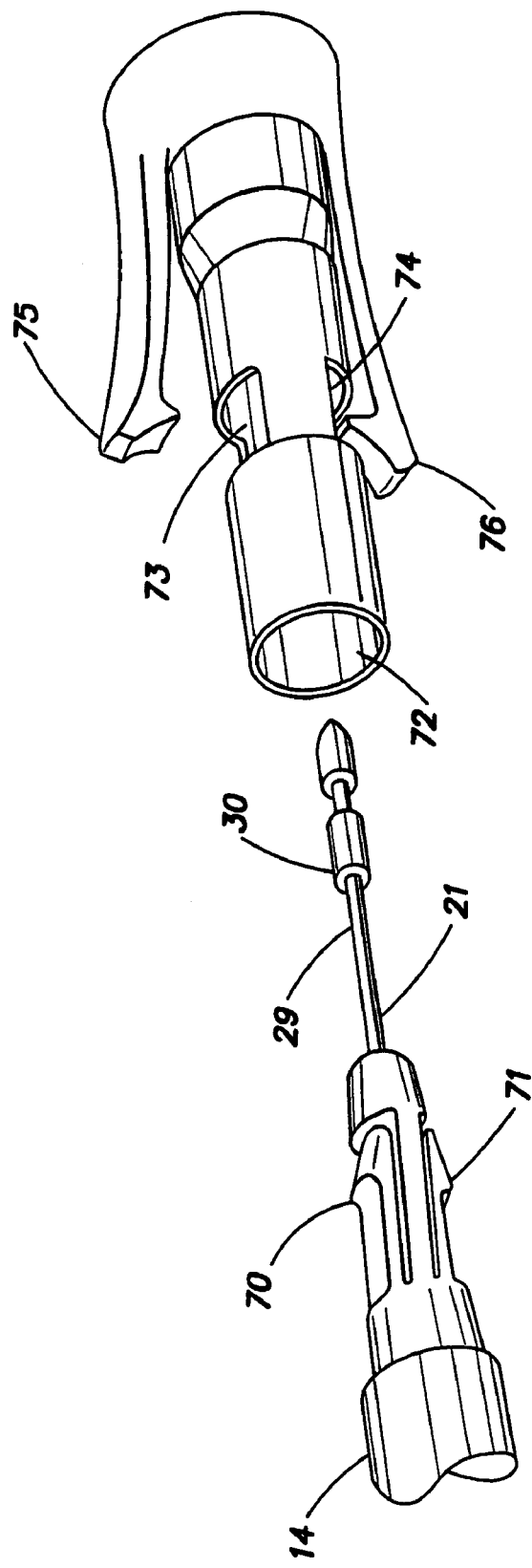
FIG. 5 depicts an exploded view of the connection between a sheath and a manipulation section of the holding device of the first embodiment.

FIG. 1 illustrates the overall configuration of the first embodiment of the present invention. Apparatus 1 comprises a first endoscope 2, holding device 11, which may be holding grasping forceps, forceps, or any other device capable of holding the digestive wall of a body cavity, extendable out of the distal end 3 of the first endoscope 2, a guide 5 running lengthwise on the outer periphery of the first endoscope 2, a second endoscope 6 to be inserted parallel to the first endoscope 2, a needle tool 40 retractable at the distal end 7 of the second endoscope 6, a sheath 84 in which the first endoscope 2 and the second endoscope 6 are retractably inserted, a suture 46 retractably insertable in a lumen 8 of the needle tool 40, suture retaining device 50, which may be forceps, suture grasping forceps, or any other device capable of grasping sutures, to be inserted in a lumen 9 of the guide 5 and movable in relation to the first endoscope 2, and a knot pusher 61 to be used with the first endoscope 2 or second endoscope 6. Each member of the first embodiment is described as follows.

FIGS. 2 to 6 depict the first endoscope 2 and holding device 11 of the first embodiment. The holding device 11 comprise a distal portion 12, a sheath 14 fixed at the proximal end of the distal portion 12 and inserted in a channel 13 of the endoscope 2, and an manipulation section 15 fixed detachably at the proximal end of the sheath 14 for operating the distal portion 12. In the distal portion 12, a pair of jaws 17a and 17b, which may be forcep jaws, are fixed pivotally with a pin 18 to a cover 16 and via links 19a and 19b to a cable anchor 20. A cable 21 is fixed to the cable anchor 20, and inserted in the sheath 14. The cable 21 is fixed detachably to a sliding part 22 of the manipulation section 15. A slider handle 23 is fixed to the sliding part 22, and is translated lengthwise in relation to the manipulation section 15.

The distal portion 12 has a larger outside diameter than the channel 13 of the first endoscope 2. The jaws 17a and 17b have a plurality of teeth 24a and 24b for grasping tissue securely, which engage each other when the jaws 17a and 17b are in a closed position. To minimize damage to tissue when it is grasped, the surface of the teeth 24a and 24b are smooth with a minimum amount of sharp edges. The jaws 17a and 17b have longitudinal grooves 25a and 25b to permit tissue to escape when it is grasped securely, and to prevent tissue from collapsing.

The slider handle 23 has a serrated part 26, which is retractable. The sliding surface 27 of the manipulation section 15 has serrations 28. Together the serrated part 26 and the serrations 28 act as ratchet mechanism.

A hook 30 is fixed to the proximal end 29 of the cable 21, and is inserted into a hole 31 of the slider handle 23. Threads 32 are formed vertically in the hole 31. The hook 30 is fixed in the hole 31 by screwing a knob 33 to engage the hook 30.

The sheath 14 has two catches 70 and 71 at the proximal end, which may be arranged diametrically from each other. The manipulation section 15 has an introduction hole 72 in the axial direction at the distal end to accommodate the sheath 14. Two engagement holes 73 and 74 are disposed within the walls of the introduction hole 72 to engage with the catches 70 and 71. Outside of each of the engagement holes 73 and 74, there are deformable latches 75 and 76, that press the catches 70 and 71 through the engagement holes 73 and 74.

Figure 7:
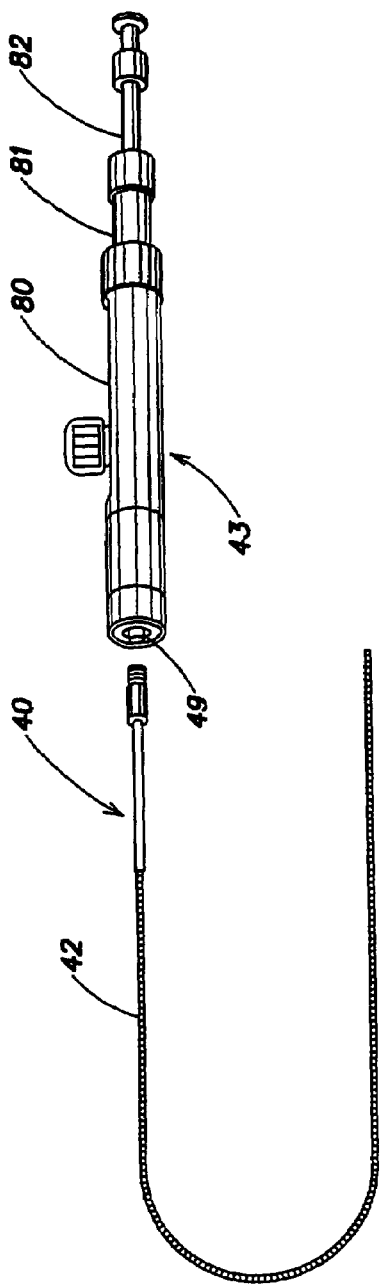
FIG. 7 depicts a needle tool of the first embodiment.
Figure 8:
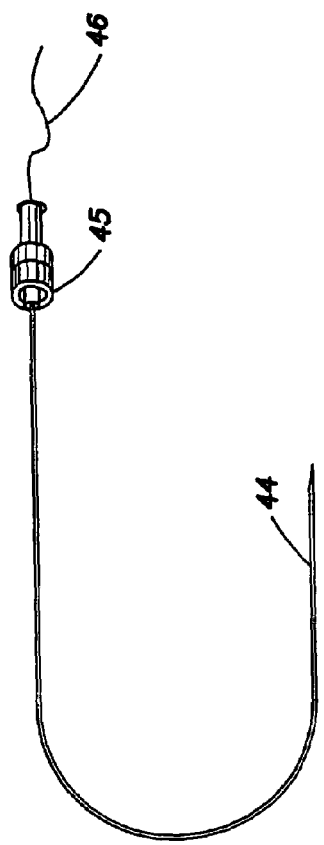
FIG. 8 depicts a needle of the first embodiment.
Figure 9:
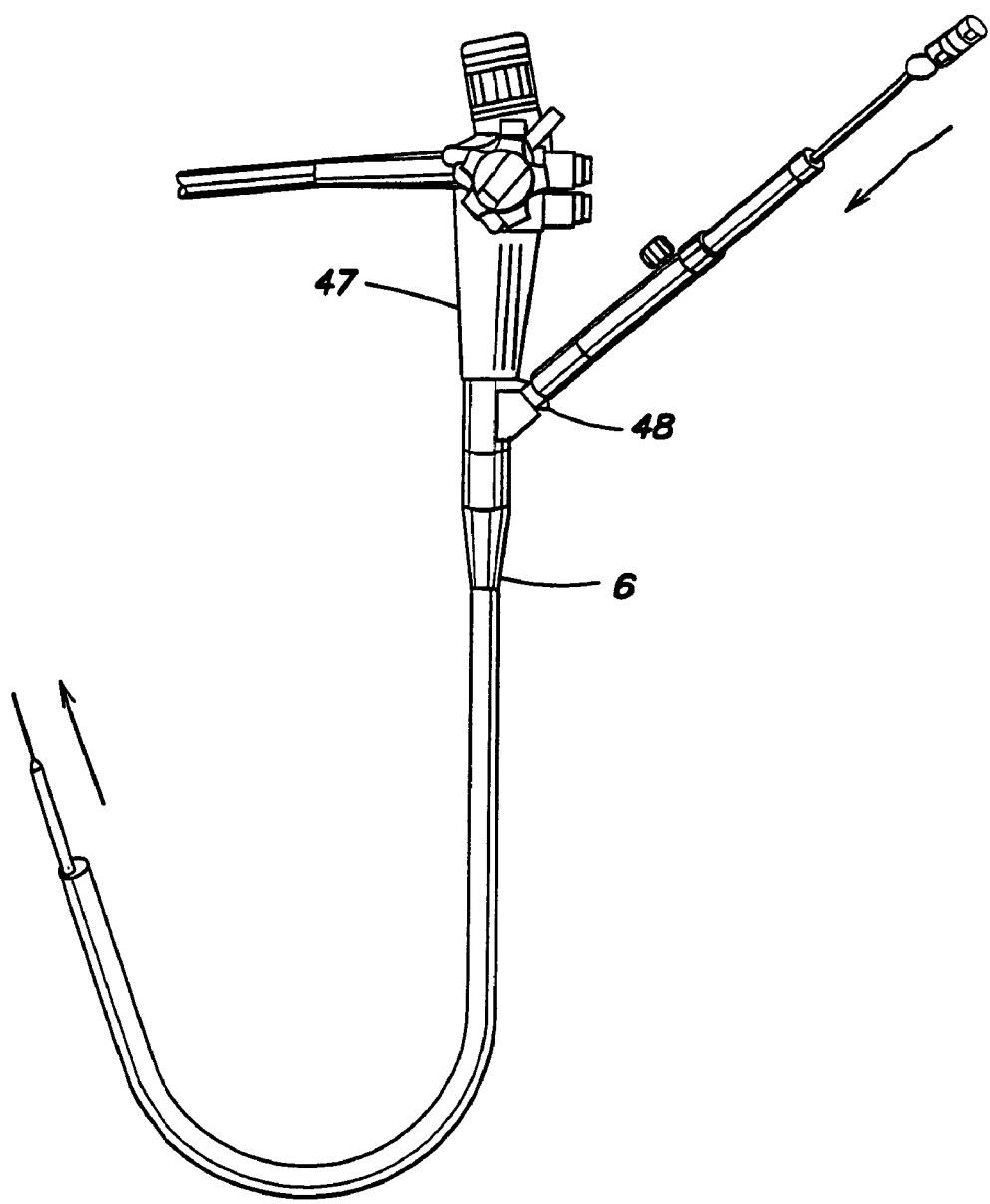
FIG. 9 depicts the needle tool, a needle, and a suture in a second endoscope of the first embodiment.

FIGS. 7 to 9 depict the second endoscope 6, needle tool 40, and suture 46 of the first embodiment. The needle tool 40 comprises a sheath 42 to be inserted in the channel 41 of the second endoscope 6, a manipulation section 43 disposed at the proximal end of the sheath 42, a needle 44 sliding in the lumen of the sheath 42, a grip 45 fixed to the proximal end of the needle 44, and a suture 46 to be inserted slidably in the lumen of the needle 44. The needle 44 may be made of stainless steel or any material having sufficient flexibility to withstand proximal pressure and adapt to the bending of the endoscope, such materials include super elastic alloys including nickel titanium alloy. The manipulation section 43 comprises a body 80, a sheath sliding section 81, and a needle sliding section 82, which slides in the longitudinal direction. The distal end of the sheath sliding section 81 is fixed to the proximal end of the sheath 42. The grip 45 of the needle 44 is fixed detachably to the proximal end of the needle sliding section 82. The manipulation section 43 has at the distal end a connecting section 49 to be fixed detachably to a channel clasp 48 of the handle 47 of the endoscope 6.

Figure 10A:
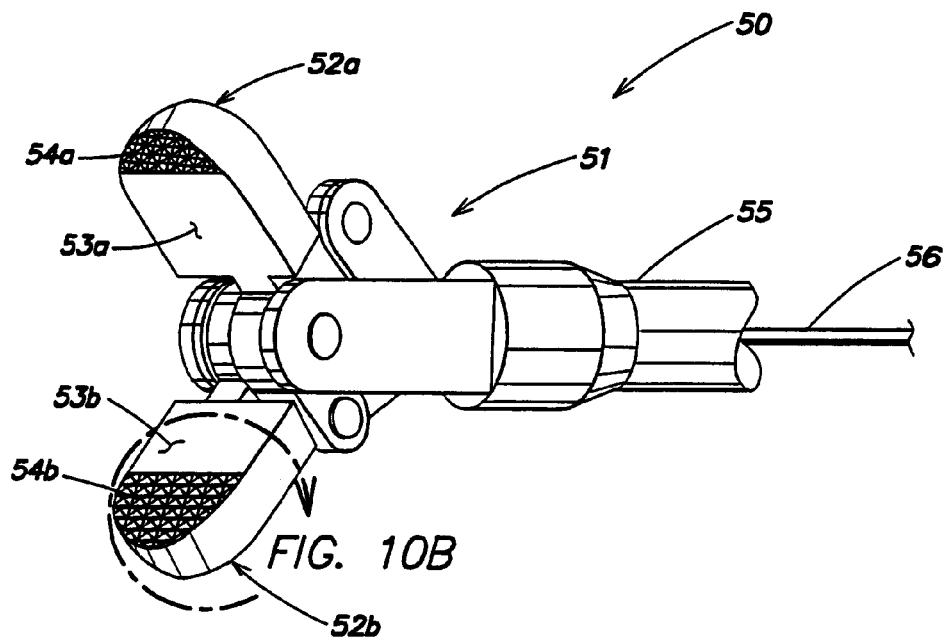
FIGS. 10A and 10B depict a detail view of the distal end of a suture retaining device of the first embodiment.
Figure 10B:
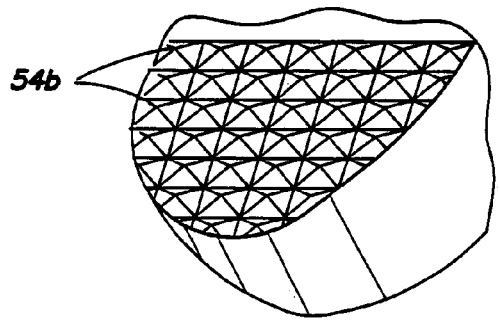

The suture 46 may be made of durable, slidable material capable of sliding smoothly in the lumen 8 of the needle 44, such as nylon monofilament or multifilament coated with fluoroplastics. FIGS. 10A and 10B depict the suture retaining device 50 of the first embodiment. The suture retaining device 50 is slidably insertable in the lumen 9 of the guide 5, which is fixed on the outer periphery of the first endoscope 2. A distal section 51 has jaws, 52a and 52b, which may be forcep jaws with an opening and closing position. The jaws 52a and 52b each have a plurality of small protrusions 54a and 54b for preventing the suture 46 from slipping off the grasping surfaces 53a and 53b. The distal section 51 has, at the proximal end, a sheath 55 following the curve of the first endoscope 2 and a wire 56 capable of translating longitudinally in the sheath 55. The wire 56 has a slider handle 57 at the proximal end, and the sheath 55 has a manipulation section 58 at the proximal end. The slider handle and the manipulation section have, like the holding device 11, a serrated part (not shown) and serrations (not shown), which together act as a ratchet mechanism.

Figure 11:
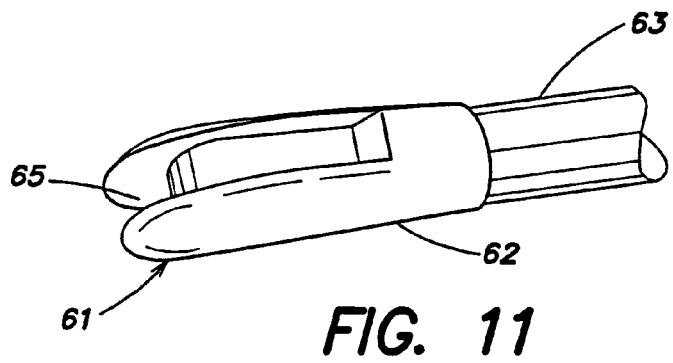
FIG. 11 depicts a knot pusher of the first embodiment.

FIG. 11 depicts a knot pusher 61 comprising a distal end 62, a sheath 63 to be inserted in the channel 13 or 41 of the first endoscope 2 or second endoscope 6, and a knob 64 for pressing the distal end 62 in the longitudinal direction. The distal end 62 has a slit 65 for engaging the suture 46.

FIGS. 2 to 9 further depict assembly of the first embodiment. The hook 30, the cable 21, and the sheath 14 are inserted into the channel 13 from the distal end 3 of the first endoscope 2. Next, the hook 30, extending out of the proximal end of the first endoscope 2, is inserted in the hole 31 of the sliding part 22. The knob 33 of the slider handle 23 is screwed into the threads 32 in the slider handle 23 to hold and engage the hook 30 with the sliding part 22. Then, the sheath 14 is inserted in the introduction hole 72 of the manipulation section 15 to deform the catches 70 and 71 inward and diametrically to be housed in the introduction hole 72. The catches 70 and 71 deform diametrically outward to engage the engagement holes 73 and 74. At this point, the sheath 14 and the manipulation section 15 are fixed.

The guide 5 is fixed on the outer periphery 4 of the first endoscope 2 at several points using a medical tape. The suture 46 is inserted in the lumen 8 of the needle tool 40.

The grip 45 is pulled proximally so that the needle 44 or the suture 46 is withdrawn in the distal end of the needle tool 40. The sheath 42 is inserted from the channel clasp 48 of the second endoscope 6 to the channel 41 until the distal end of the sheath 42 extends out of the distal end of the endoscope 6. Then the body 80 is fixed to the channel clasp 48 of the endoscope 6.

Figure 12:
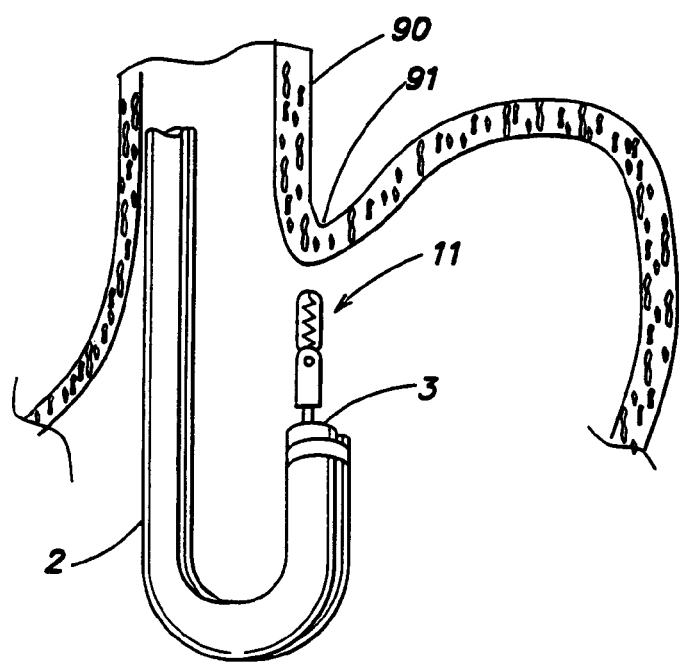
FIGS. 12 to 27 depict steps of a treatment method using the first embodiment.
Figure 13:
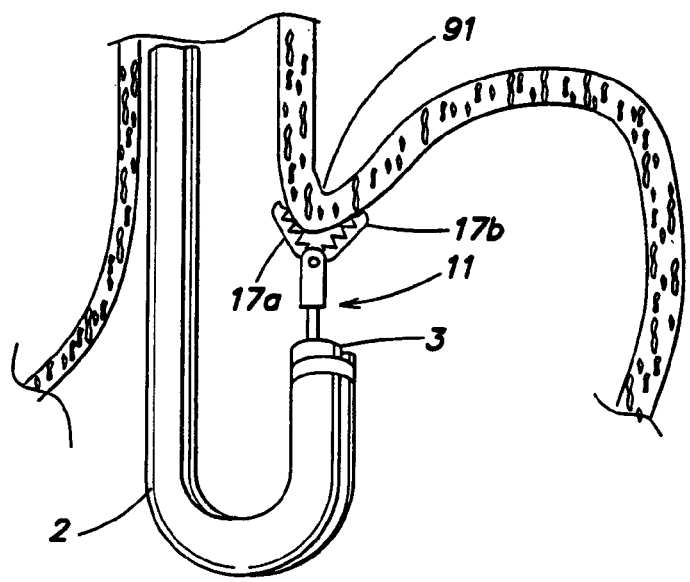
Figure 14:
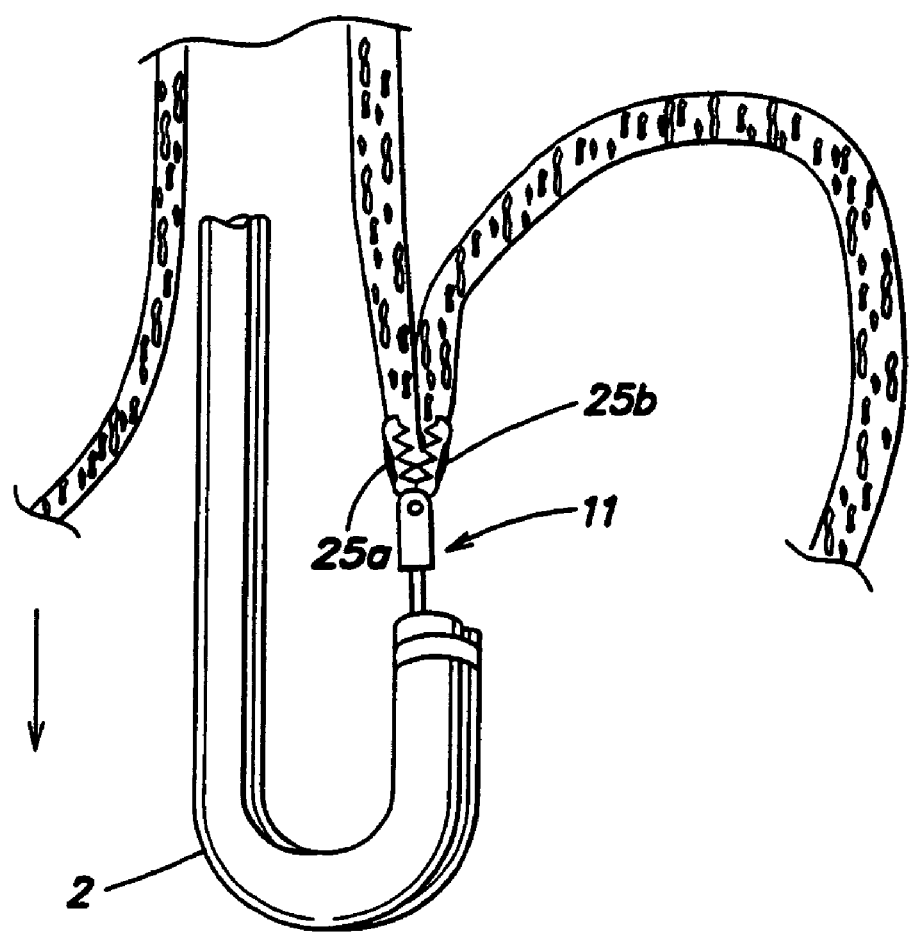
Figure 15A:
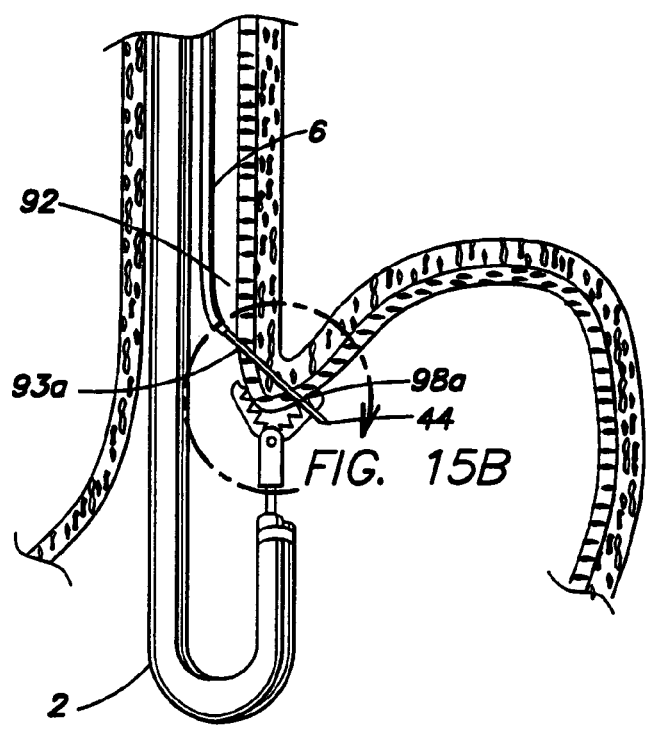
Figure 15B:
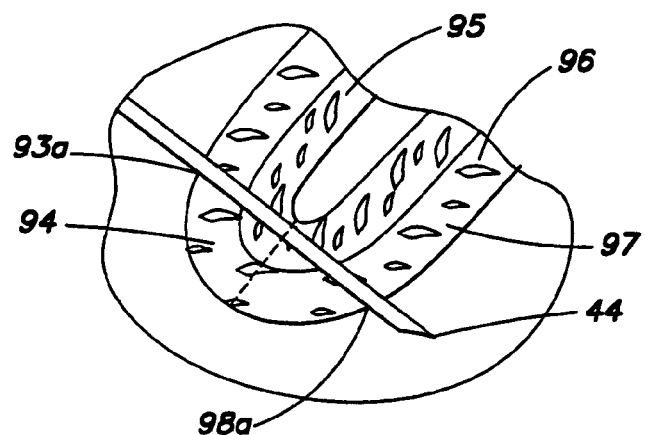
Figure 16A:
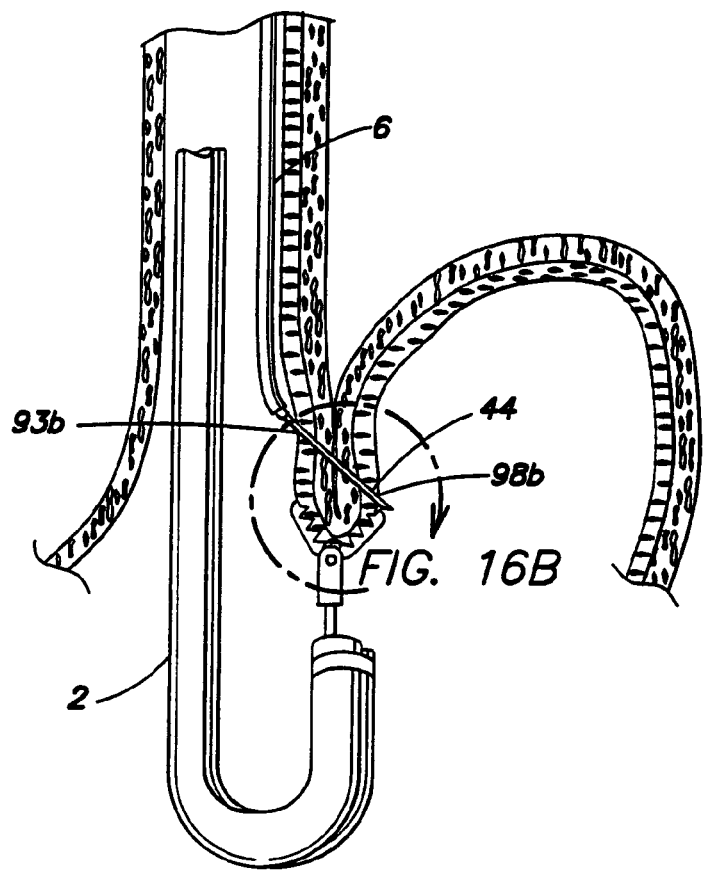
Figure 16B:
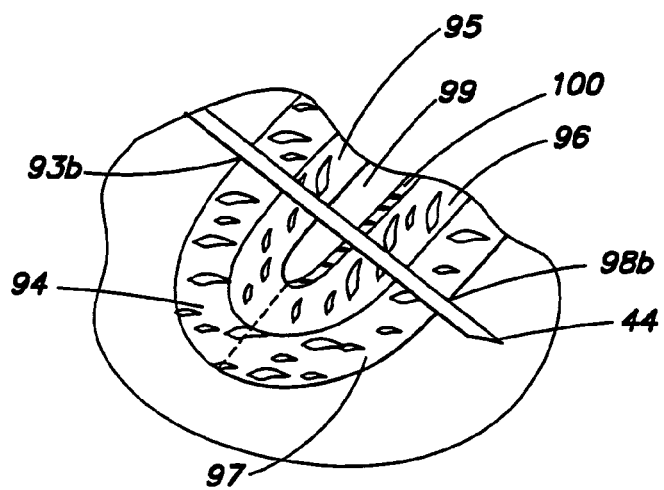

FIGS. 12 to 14 depict holding and suspending of the cardia using the apparatus of the first embodiment. The sheath 14 of the holding device 11 is drawn proximally to withdraw only the distal portion 12 in the distal end 3 of the first endoscope 2. The first endoscope 2 covered by the sheath 84 is inserted into the body cavity of a patient. Because the distal portion 12 is also covered by the sheath 84, the endoscope 2 can be inserted without any trauma of to the patient's tissue. The first endoscope 2 is inserted into the stomach of the patient, and withdrawn from the sheath 84, then, the distal end 3 is bent upwards to face the cardia 90.

The slider handle 23 is pressed distally against the manipulation section 15 (not shown in FIGS. 12 to 14). The hook 30, the cable 21, and the cable anchor 20 are translated distally to rotate the links 19a and 19b, and in turn, the jaws 17a and 17b around the pin 18 to open the jaws 17a and 17b. The sheath 14 is moved forward to bring the jaws 17a and 17b into contact with the tissue 91 in the side of the greater curvature of the stomach at the cardia 90.

The slider handle 23 is pulled proximally to close the jaws 17a and 17b. The tissue 91 is held and pressed by the jaws 17a and 17b, but will not collapse to overflow from the longitudinal grooves 25a and 25b or because the teeth 24a and 24b are not sharp. The serrated part 26 of the slider handle 23 is extended against the sliding surface 27 of the manipulation section 15, and engaged with the serrations 28 to limit distal movement of the slider handle 23. The jaws 17a and 17b hold and fix the tissue 91, once it is held, even if the slider handle 23 or the manipulation section 15 is not held by physician.

The first endoscope 2 is inserted deeply into the body to suspend the first endoscope 2 and the holding device 11. The distal portion 12 has a larger outside diameter than the channel 13 of the first endoscope 2. The jaws 17a and 17b are wide and long, and the tissue 91 is suspended and fixed by the jaws 17a and 17b.

FIGS. 15A, 15B, 16A and 16B depict penetrating the gastric and esophagus walls using the first embodiment. The second endoscope 6 is inserted parallel to the first endoscope 2. The distal end of the second endoscope 6 is positioned at a point 92 above the junction between the stomach and the esophagus while it is observed by the second endoscope 6. Then the second endoscope 6 is manipulated to bend the distal end 7 slightly toward the side of the greater curvature of the stomach. The sliding section 81 is moved distally against the body 80 to extend the sheath 42 out of the distal end 7 of the second endoscope 6, and to press an entering point 93a.

The grip 45 is pressed forward to extend the needle 44 out of the sheath 42. Because the greater curvature of the stomach at the cardia 90 has already been held by the holding device 11 and suspended with the first endoscope 2, the needle 44 pierces from the entering point 93a through the mucous membrane 94, continuing at least through the proper muscularis 95 of the esophagus, then through the proper muscularis 96 of the stomach, and then through the mucous membrane 97 of the stomach, and exiting out of an exiting point 98a of the cardia.

Next, the first endoscope 2 is inserted deeper in the body, and the tissue 91 is suspended lower, the needle 44 passes the entering point 93b, the mucous membrane 94 of the esophagus, the proper muscularis 95 of the esophagus, the abdominal cavity 99, the serous membrane 100 of the stomach, the proper muscularis 96 of the stomach, the mucous membrane 97 of the stomach, and the exiting point 98b at the cardia.

The first endoscope 2 checks that the needle 44 comes out in the stomach.

Figure 17:
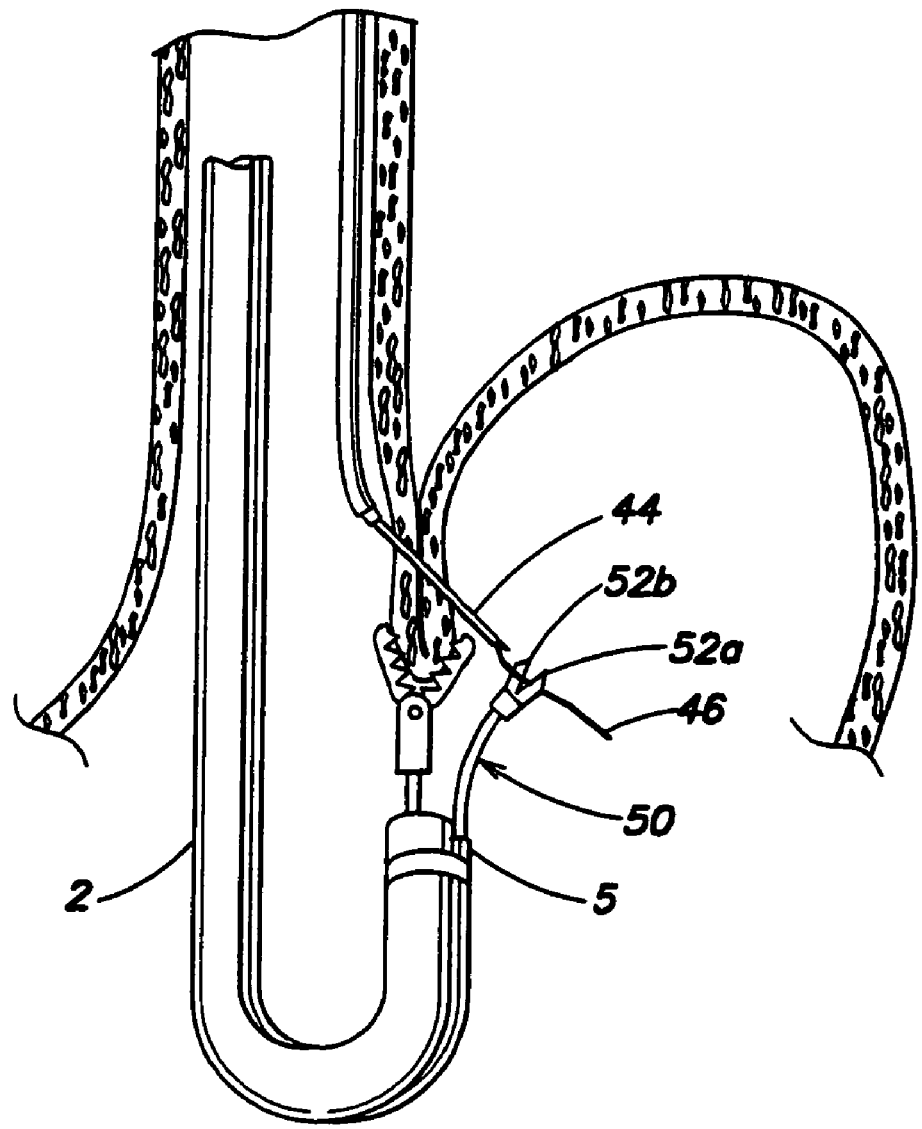
Figure 18:
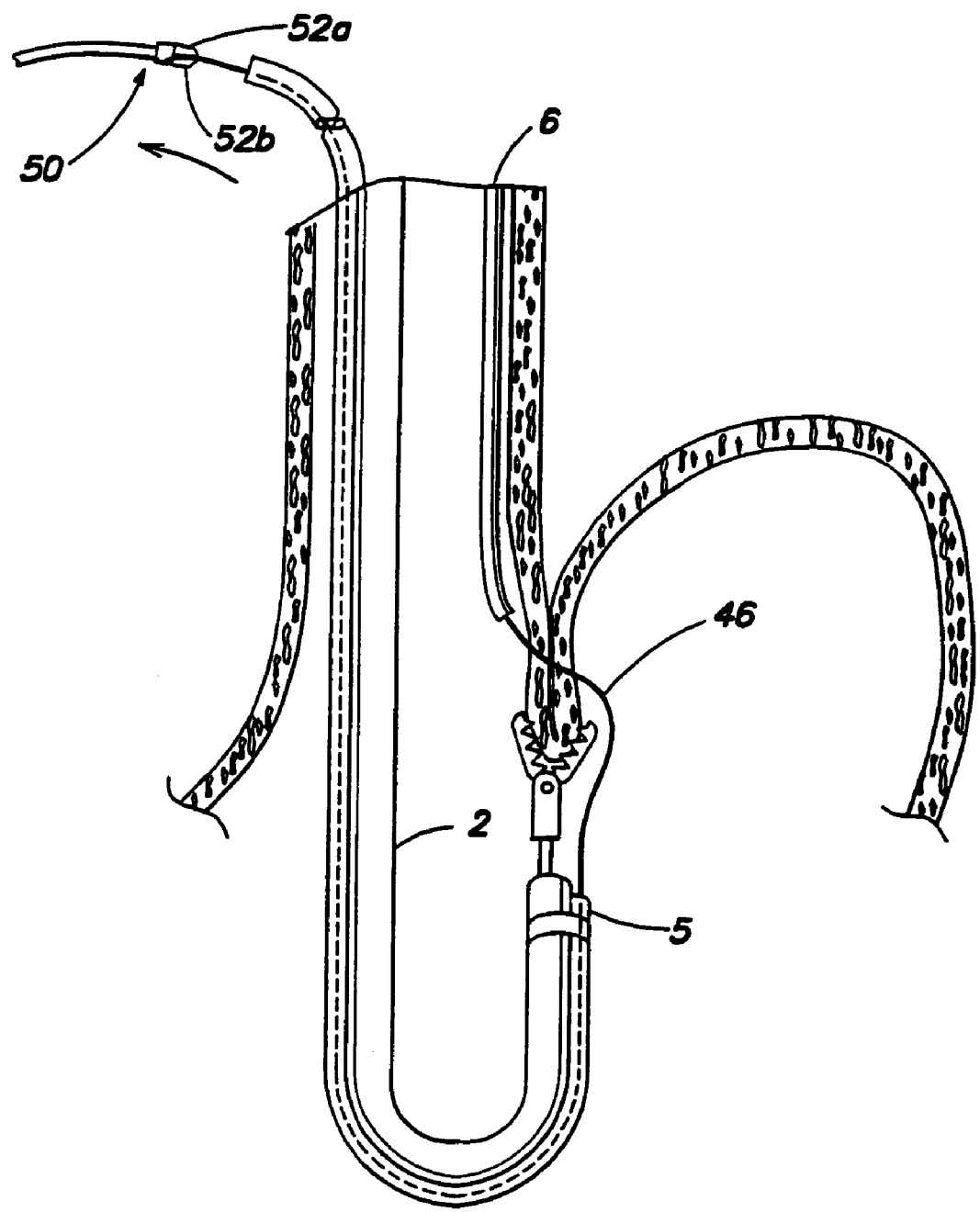
Figure 21:
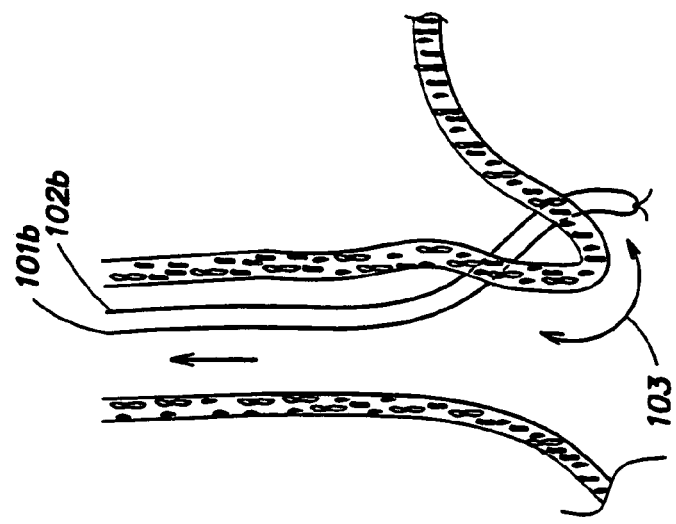
Figure 20:
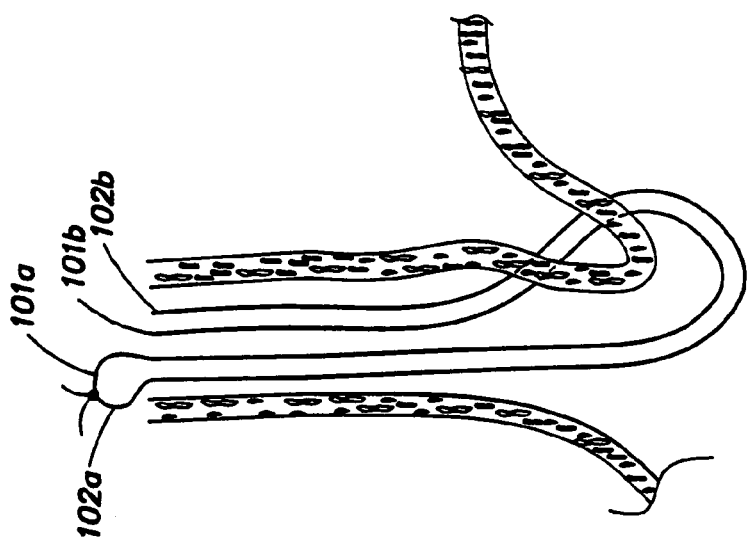

FIGS. 17 and 18 depict inserting and pulling the suture with the first embodiment. The suture retaining device 50 is inserted in the guide 5 and extended out in the stomach of the patient. The process is observed by the first endoscope 2. The suture 46 is pressed in the needle 44, and extended out in the stomach. With the suture retaining device 50 drawn into contact with the suture 46, the slider handle 57 is moved forward against the manipulation section 58 to open the jaws 52a and 52b. The suture 46 is held by the jaws 52a and 52b. The slider handle 57 is moved proximally against the manipulation section 58 to close the jaws 52a and 52b. The suture 46 is held by the small protrusions 54a and 54b on the grasping surfaces 53a and 53b of the jaws 52a and 52b. The jaws 52a and 52b are designed to minimize the chances that the suture 46 will slip off, or be cut or damaged. When the serrated part of the slider handle 57 is engaged with the serrations of the manipulation section 58, distal movement of the slider handle 57 will not be limited. Therefore, the jaws 52a and 52b hold and fix the suture 46 with handsfree operation of the slider handle 57 or the manipulation section 58. Next, the suture retaining device 50 is withdrawn from the guide 5 together with the suture 46. The serrated part 26 of the holding device 11 is lifted to disengage from the serrations 28. The slider handle 23 is moved forward to open the jaws 17a and 17b to release the tissue 91.

Figure 19:
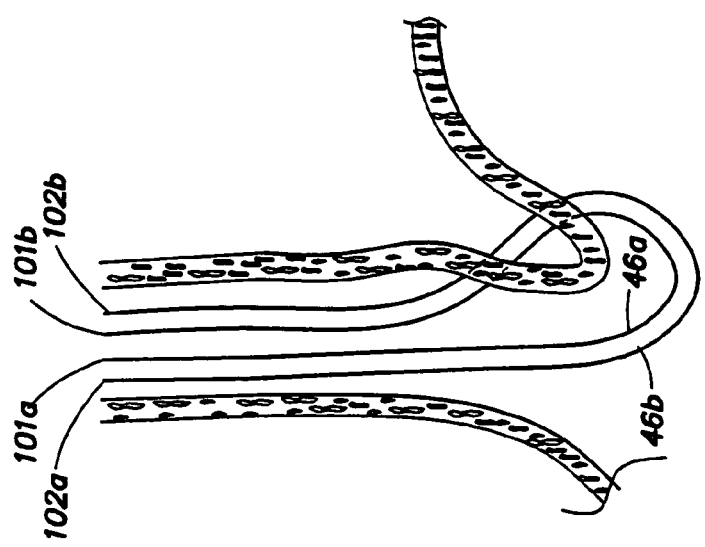
Figure 23:
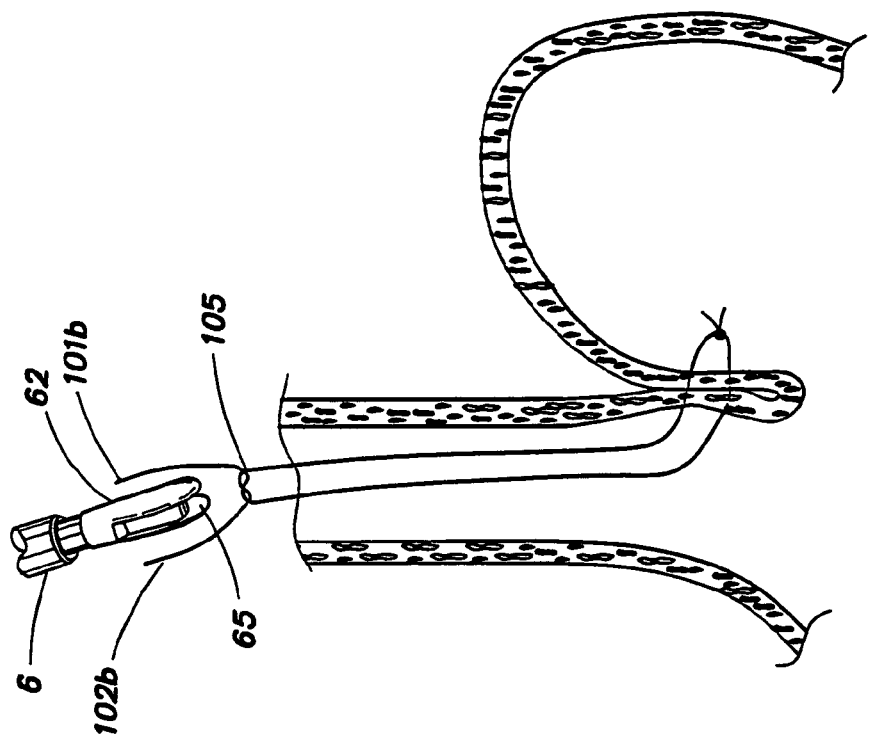
Figure 22:
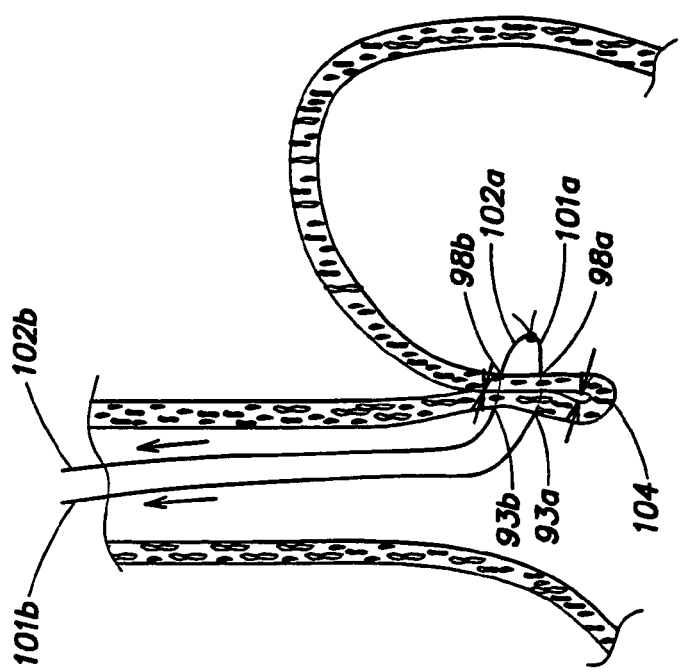

The steps illustrated in FIGS. 17 and 18, and discussed above, are repeated to pass two sutures 46a and 46b through the following points: from outside the body, the channel 13 of the first endoscope 2, the patient tissue of the esophagus and the stomach, inside the guide 5, outside the body. The endoscopes 2 and 6 are withdrawn with the sutures 46a and 46b remaining in the body cavity. The resulting configuration is shown in FIG. 19.

FIGS. 19 to 22 depict formation of the artificial valve using the first embodiment. The suture 46a has ends 101a and 101b; the suture 46b has ends 102a and 102b. The ends 101a and 102a, which are on the side of the stomach, are tied to each other outside the patient's body. The free ends 101b and 102b, which are on the side of the esophagus, are pulled to draw the ends 101a and 102a into the body cavity. The ends 101a and 102a adjoin, and are fixed at exiting points 98a and 98b of the stomach. Then the ends 101b and 102b are pulled further to bring the gastric wall near the exiting points 98a and 98b close to entering points 93a and 93b in the esophagus. Thus, a junction 103 of the stomach and the esophagus between the exiting points 98a and 98b and the other entering points 93a and 93b is shortened to form an internal protrusion 104.

Figure 25:
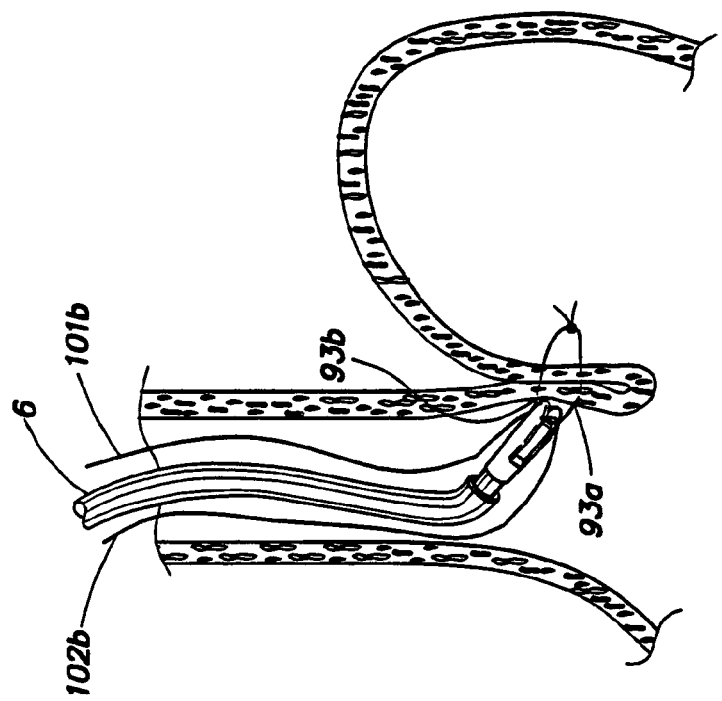
Figure 24:
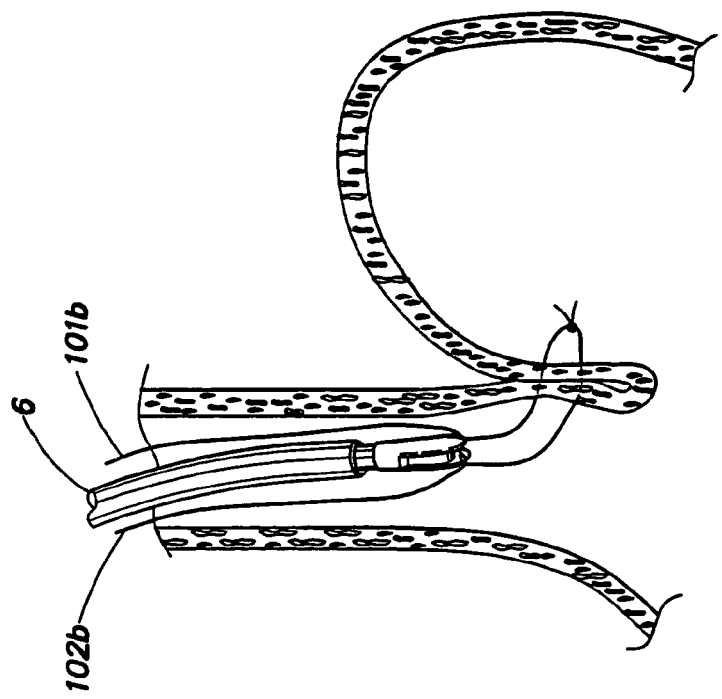
Figure 27:
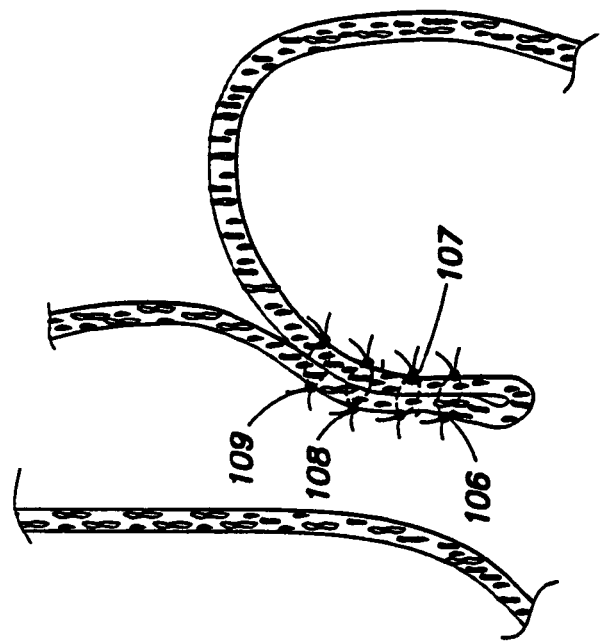
Figure 26:
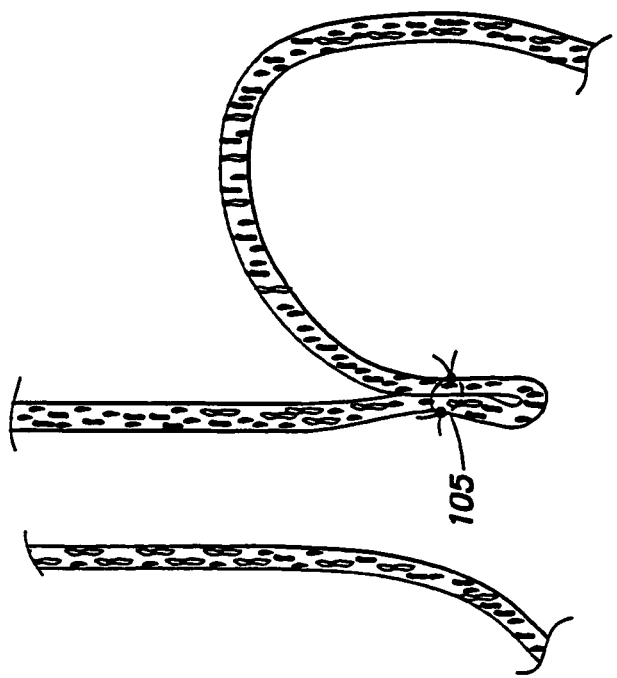

FIGS. 23 to 27 depict fixing the sutures with the first embodiment. The ends 101b and 102b of the sutures 46a and 46b are tied outside the body to form a knot 105. The knot pusher 61 is inserted in the channel 41 of the second endoscope 6, and its distal end 62 is extended out of the distal end of the second endoscope 6. With the knot 105 engaged on the slit 65, the second endoscope 6 and the knot pusher 61 are inserted into the body cavity. Then, the ends 101b and 102b of the sutures are pulled to move the knot 105 and the second endoscope 6 into the body cavity. As seen in FIG. 25, when the knot 105 reaches the entering points 93a and 93b of the esophagus, the distal end 62 is pressed against the entering points 93a and 93b while the ends 101b and 102b are pulled to fix the knot 105. The above step is repeated several times to prevent the knot 105 from loosening. After the knot 105 is fixed firmly, the second endoscope 6 and the knot pusher 61 are withdrawn out of the body cavity. The excess sutures 46a and 46b beyond the knot 105 are cut using endoscopic scissors (not shown), and are collected to finish the process. Depending on the patient's symptoms, the above process will be repeated to form a plurality of stitches 106 to 109, as illustrated in FIG. 27, to form a larger protrusion.

The holding device 11 inserted in the first endoscope 2 allows suspension of the tissue 91 while it is held and fixed securely. Because the distal portion 12 is formed larger than the channel 13 of the endoscope 2, the jaws 17a and 17b are long and wide enough to hold and suspend a large area of the tissue 91 without damaging it. Therefore, the needle 44 can pierce deep into the proper muscularis. A large protrusion including the proper muscularis of the stomach and the esophagus is formed as artificial valve for preventing reflux effectively.

Because the holding device 11 extends out of the distal end of the endoscope 2, the jaws 17a and 17b touch the tissue 91 easily while it is observed by the first endoscope 2. The process is simple for the operator to perform, and requires a short time.

Because both the second endoscope 6 and the needle tool 40 are provided separately from both the first endoscope 2 and the holding device 11, the operator independently controls suspension of the cardia and the positions of the entering points 93a and 93b to form valves of varying size according to the patient's particular symptoms.

In the first embodiment, the second endoscope or the needle is provided separately from the first endoscope or the fixing means. The operator controls at discretion suspension of the tissue or the entering point of the needle to form a valve of different size according to the symptom of a patient.

Figure 28:
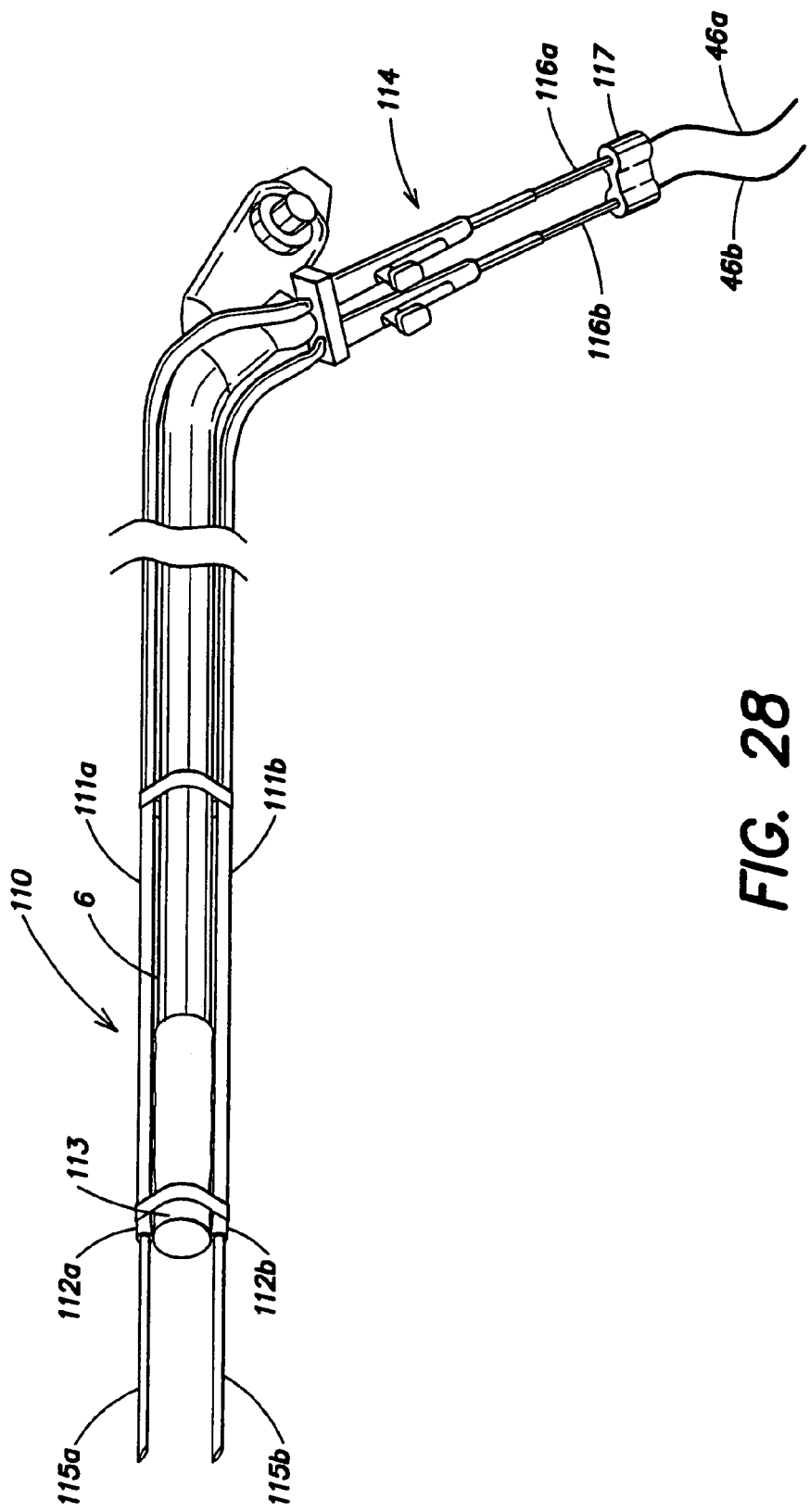
FIG. 28 depicts a second embodiment of the present invention.
Figure 30:
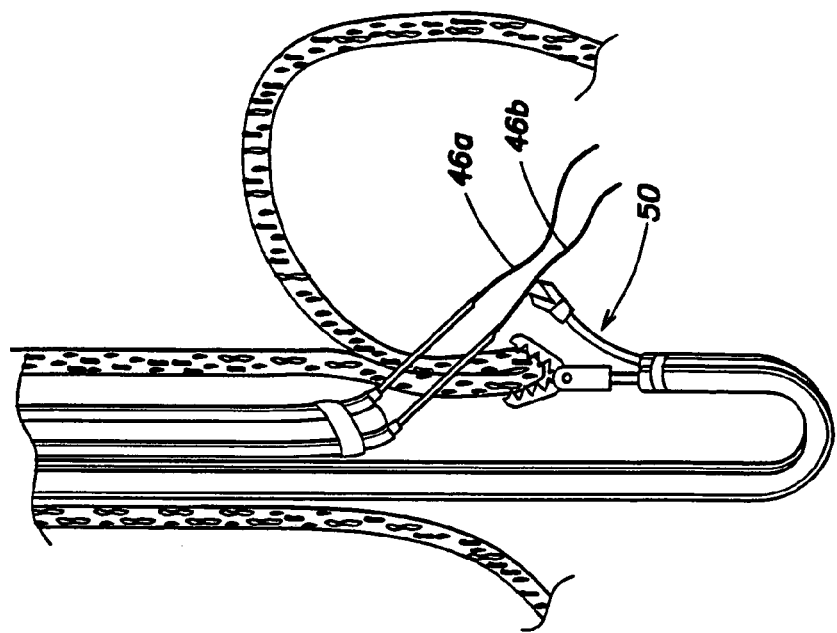
FIGS. 29 to 30 depict a treatment method using the second embodiment.
Figure 29:
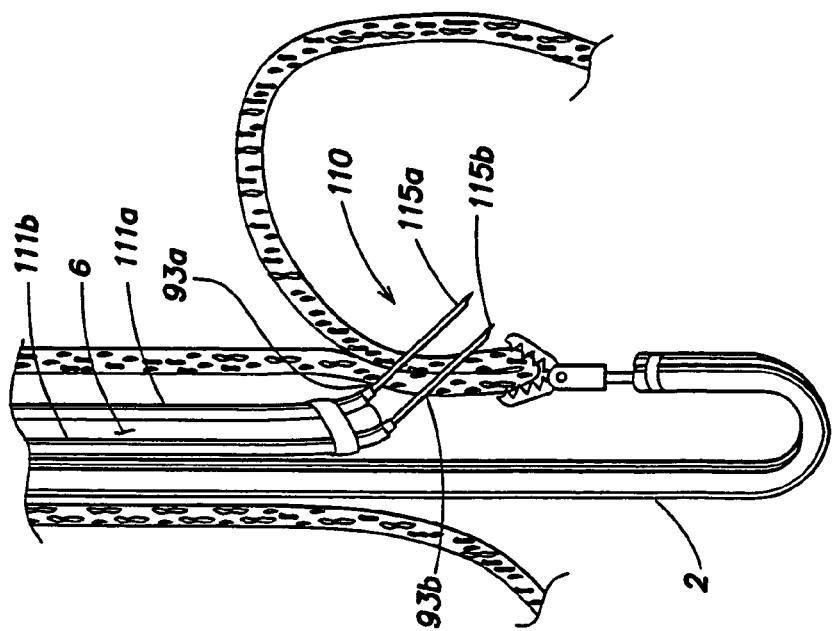

FIGS. 28 to 30 depict the second embodiment of the present invention. The same components as the first embodiment are indicated by the same numbers, and their description will be omitted.

In the second embodiment, a needle tool 110 is composed as follows. Two sheaths 111a and 111b are fixed at the distal ends 112a and 112b parallel to the distal end 113 of the second endoscope 6. The sheaths 111a and 111b are fixed at the proximal portion on the outer periphery of the second endoscope 6 using medical tape at several points. The two sheaths 111a and 111b are fixed to the manipulation section 114 and accommodate needles 115a and 115b, which slide inside. Grips 116a and 116b are fixed to the proximal ends of the needles 115a and 115b and connected to connecting section 117 which is detachable.

After the first endoscope 2 or the holding device 11 holds and suspends the tissue 91, the endoscope 6 and the needle tool 110 fixed to the endoscope 6 are inserted into the body cavity of a patient. The endoscope 6 is operated to bring the distal ends of the sheaths 111a and 111b to contact with the entering points 93a and 93b and press the grips 116a and 116b to pierce the needles 115a and 115b.

The sutures 46a and 46b extend out of the needles 115a and 115b and are held and collected by the suture retaining device 50.

In addition to the features of the first embodiment, the second embodiment also is capable of inserting two sutures 46a and 46b are inserted at one time. In contrast, using the first embodiment an operator must set the appropriate direction and position of the second entering point 93b relative to the first entering point 93a. This takes more time and is more difficult to perform. The second embodiment is simpler in operation and takes much shorter time than the first embodiment because the two sutures 46a and 46b are inserted parallel to a certain distance at one time.

Figure 31:
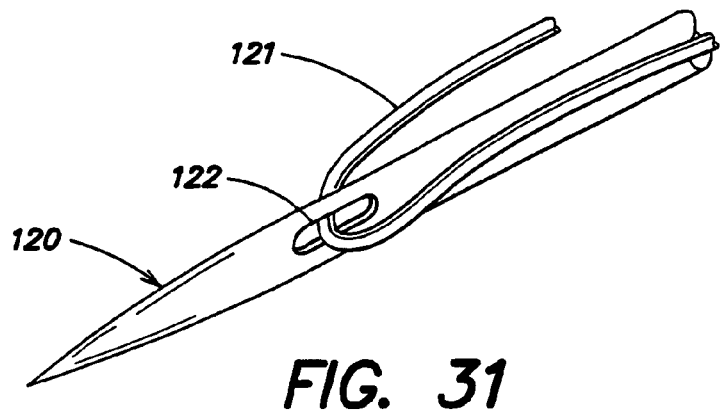
FIG. 31 depicts a third embodiment of the present invention.
Figure 32:
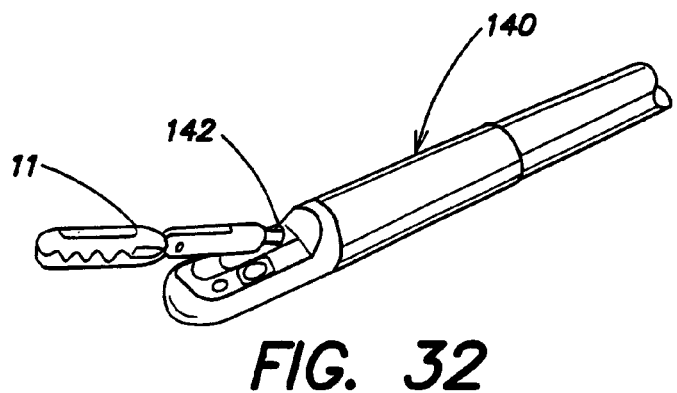
FIGS. 32 to 35 depict a fourth embodiment of the present invention.
Figure 33:
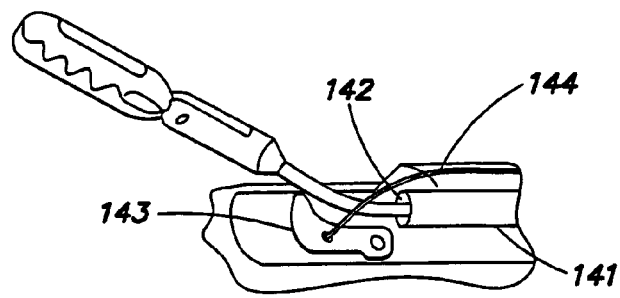
Figure 34:
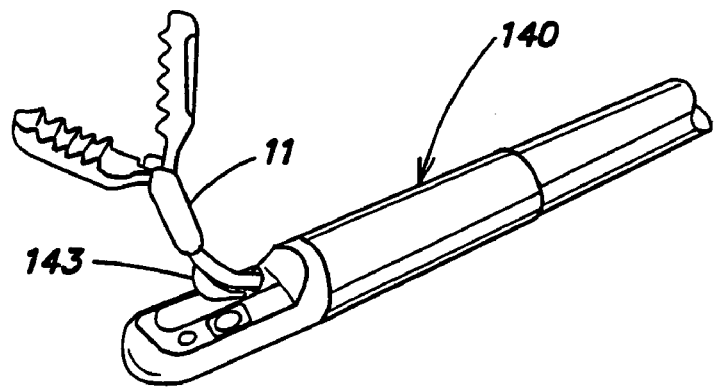
Figure 35:
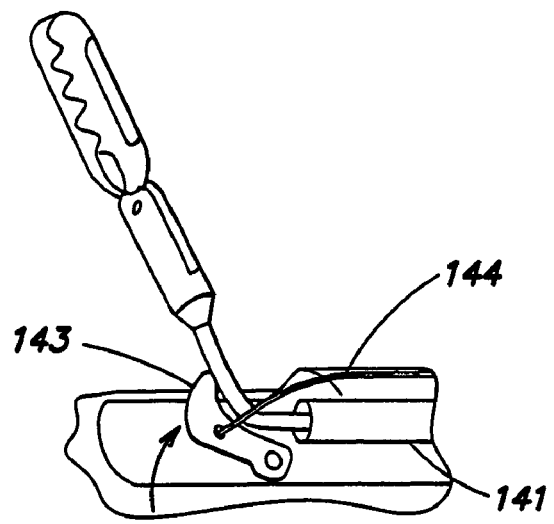
Figure 36:
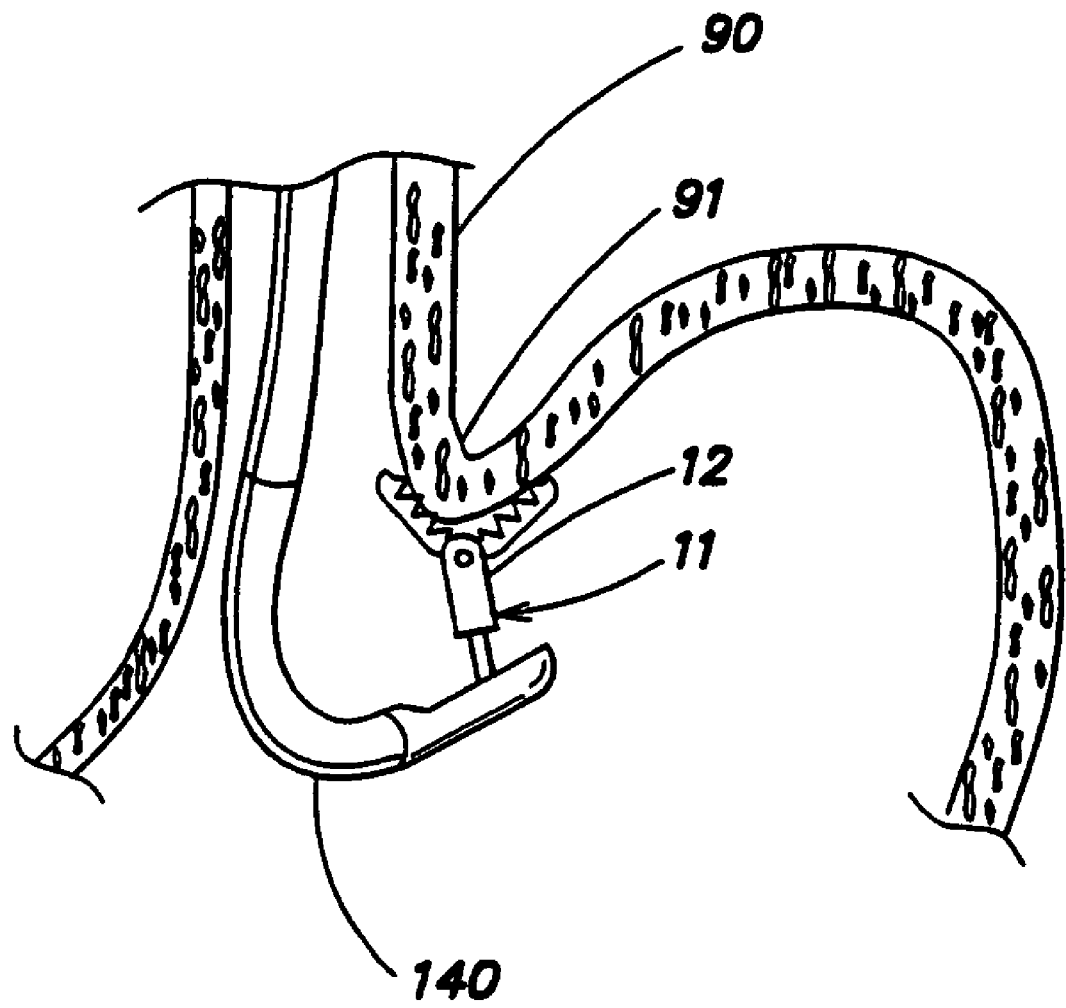
FIG. 36 depicts a treatment method using the fourth embodiment.
Figure 37:
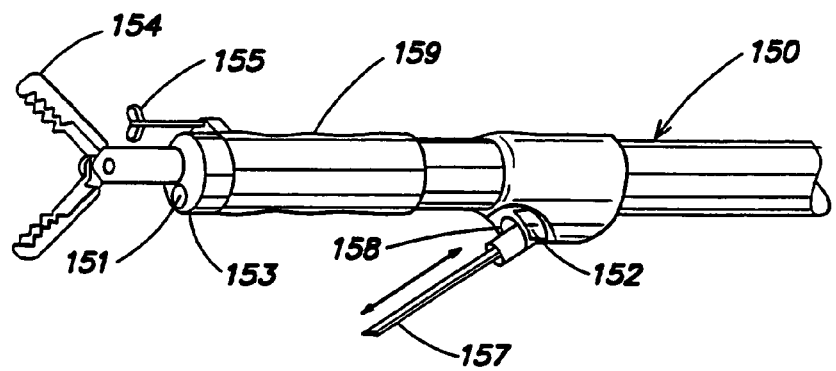
FIGS. 37 to 39 depict a fifth embodiment of the present invention.
Figure 38:
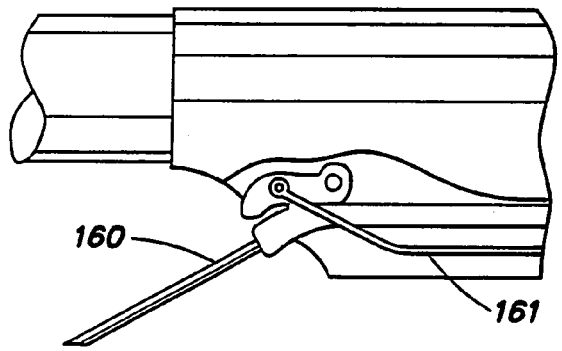
Figure 39:
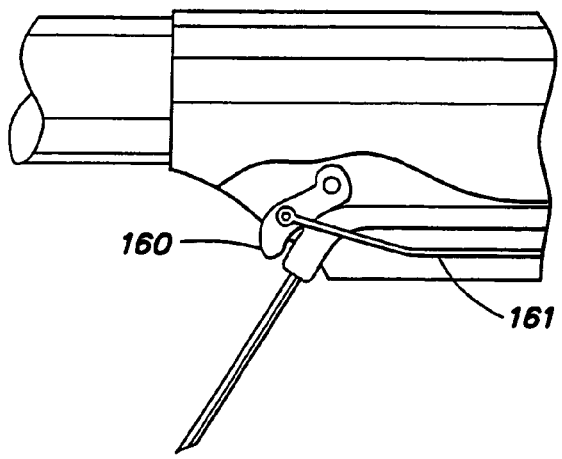
Figure 40:
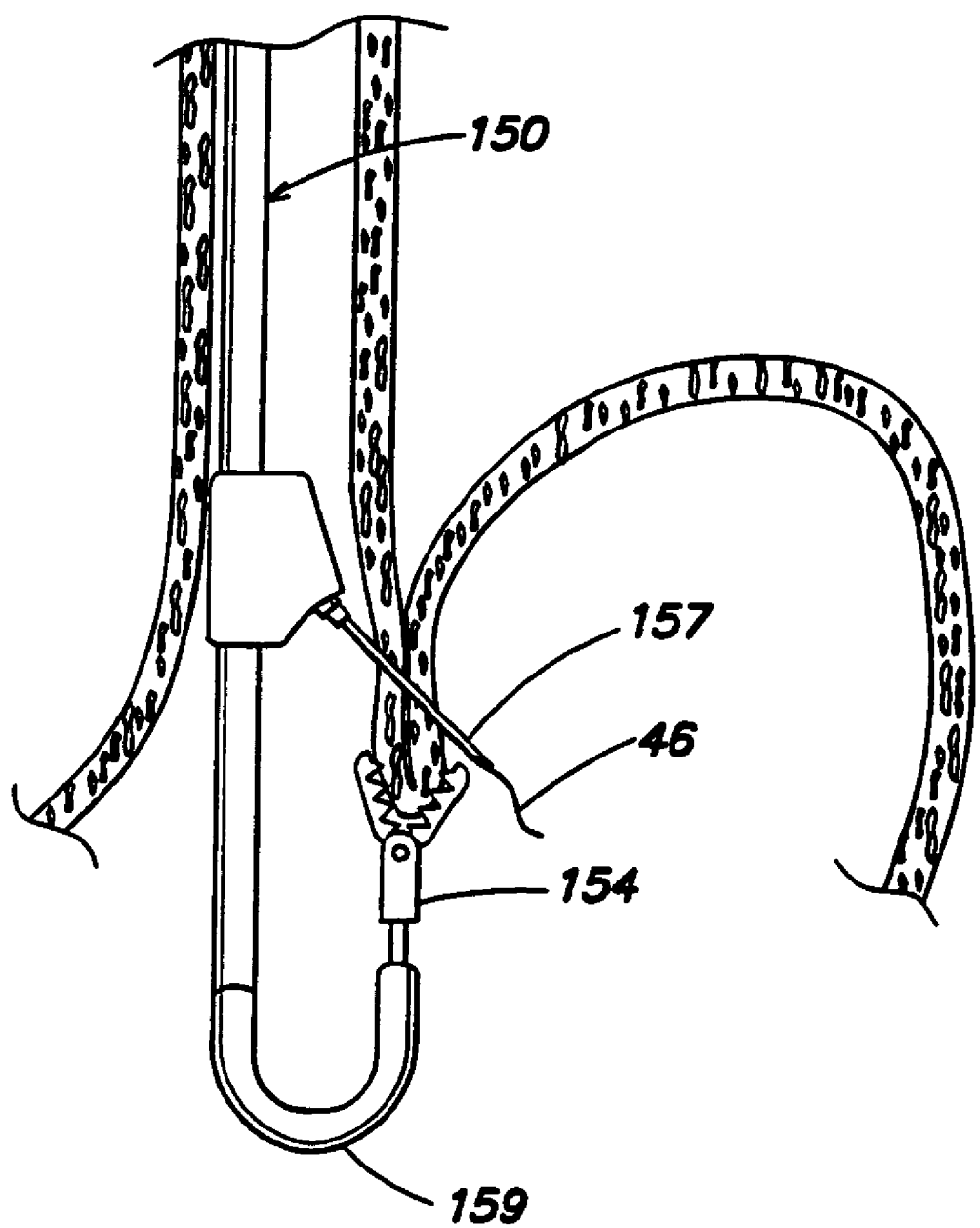
FIG. 40 depicts a treatment method using the fifth embodiment.
Figure 41:
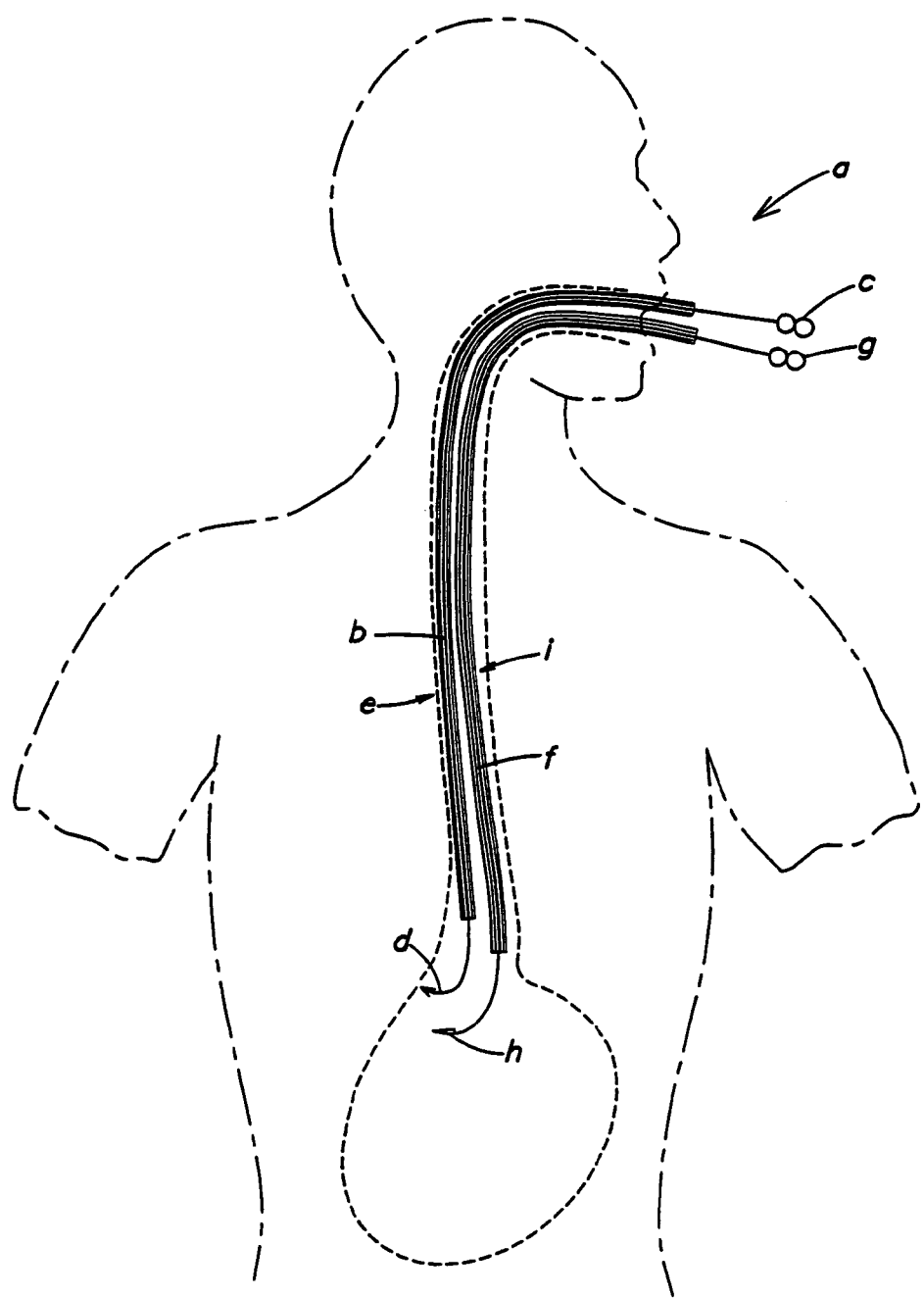
FIG. 41 depicts FIG. 3 of U.S. Pat. No. 5,887,594.
Figure 45:
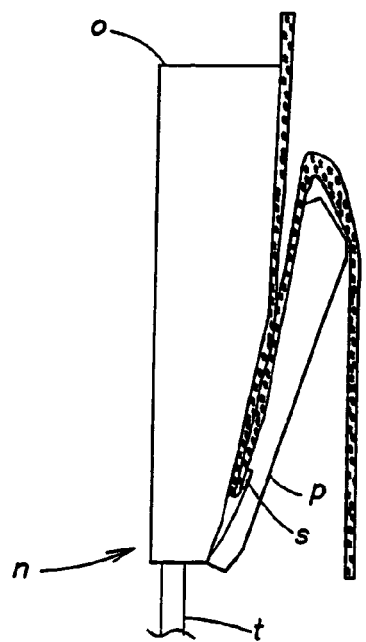
Figure 46:
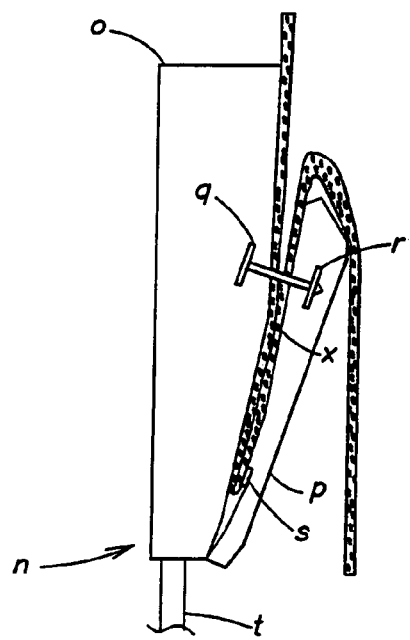

FIG. 31 depicts the third embodiment of the present invention. The same components as the first embodiment are indicated by the same numbers, and their description will be omitted.

In the third embodiment, a needle 120 does not have a lumen. Instead, a suture 121 is inserted and fixed in a through hole 122 of the needle 120.

The needle 120 pierces the tissue with the suture 121 inserted and fixed in the through hole 122. The suture grasping forceps 50 pulls the suture 121 out of the through hole 122 and removed through the guide 5 out of the body.

In addition to the effect of the first embodiment, because it is not necessary to insert the suture 121 in the needle, the needle 120 is thinner than the hollow needle 44 in the first embodiment. The needle 120 can be tapered to have a sharp tip, which pierces the tissue with smaller force to improve operability.

FIGS. 32 to 36 depict the fourth embodiment of the present invention. The same components as the first embodiment are indicated by the same numbers, and their description will be omitted.

In the forth embodiment, an endoscope 140 has an optical system capable of viewing in the side direction. A channel 141, which opens on the side, has an elevator 143 near a distal exit hole 142 for changing the direction of a tool, such as the holding device 11, as it exits the distal exit hole 142. The orientation of the tool exiting the distal exit hole 142 can be changed from the axial (axis of the endoscope 140) direction to the side direction by advancing or withdrawing a wire 144 fixed to the elevator 143.

The holding device 11 is mounted to the endoscope 140 and inserted into the stomach of a patient. The distal end of the endoscope 140 is rotated by about 90 degrees to observe the cardia 90. The wire 144 is pulled to rotate and lift the elevator 143, thus directing the distal portion 12 of the grasping forceps toward the cardia. The grasping forceps 11 are operated to grasp the target tissue 91.

In addition to the effect of the first embodiment, without inversion of the endoscope 140 in the stomach, the front view of the cardia 90 is observed using the endoscope 140 and the holding device 11 grasps and fixes the target tissue. Therefore, even if a patient has lost a part of the stomach due to another disease, and the stomach is too small to allow inversion of the endoscope 2, the present invention is effective to treat gastroesophageal reflux disease.

FIGS. 37 to 40 depict the fifth embodiment of the present invention. The same components as the first embodiment are indicated by the same numbers, and their description will be omitted.

In the fifth embodiment, the first and second endoscopes 2 and 6 are replaced by an integrated endoscope 150. The endoscope 150 has a first optical system 151 and a second optical system 152. The endoscope 150 has the first optical system 151 and holding device 154 at the distal end 153. A suture retaining device 155 is mounted retractably at the distal end 153.

The second optical system 152 as well as an exiting hole 158 of a needle 157 is provided at the proximal portion of the distal bendable section 159 of the endoscope 150 and is movable in the longitudinal direction. The exiting hole 158 is disposed near the elevator 160, and is rotated by a wire 161 fixed to the elevator 160 to change the exiting direction.

The endoscope 150 is inserted into the body of a patient until the distal end 153 enters the stomach. The endoscope 150 is manipulated to bend the distal bending section 159 to invert the distal end 153 so that it faces a direction substantially upwards. After the first optical system 151 observes the cardia 90, an actuator opens grasping forceps 154 to touch the tissue 91. Then the actuator closes the forceps 154 to fix the tissue 91. Next, the endoscope 150 is advanced deeper to suspend the cardia 90.

The second optical system 152 and the exiting hole 158 are moved in the longitudinal direction. While the area above the junction between the stomach and the esophagus is observed, the elevator 160 is operated to bring the exiting hole 158 into contact with the entering point 93. The needle 157 pierces the tissue and comes out of the exiting hole 158.

The suture 46 is extended out of the needle 157, and held and fixed by the suture retaining device 155 which extends out of the distal end 153 under observation of the first optical system 151.

With the suture 46 remaining in the tissue, the endoscope 150 is withdrawn.

The effects of the fifth embodiment are similar to those of the first embodiment. In addition, because only the integrated endoscope 150 is inserted into a patient (as opposed to inserting a first endoscope 2 and a second endoscope 6 as with the first embodiment), the device is operated by one operator, and treatment is simple and takes a shorter time.

What is claimed is:

1. A tissue-piercing device for use with a flexible endoscope for suturing or ligating tissues in body cavities, said tissue-piercing device comprising:
   two flexible sleeves provided side by side substantially in parallel along the endoscope such that a predetermined distance between the sleeves at a distal end of the endoscope is larger than a width of a channel of the endoscope;
   two flexible piercing members slidably provided in the two flexible sleeves, respectively, so as to extend from a proximal end to the distal end of the endoscope;
   wherein each of the flexible piercing members comprises a needle; and
   wherein each of the two flexible sleeves comprises a distal end portion which is removably fixed to a distal end of the endoscope, and a second portion which is removably fixed to a second part of an insertion section of the endoscope, and wherein a portion of each of the two flexible sleeves extending between the distal end portion and the second portion is not fixed to the endoscope.

2. The tissue-piercing device according to claim 1, wherein each of the needles includes a hollow space extending therethrough.

3. The tissue-piercing device according to claim 1, further comprising a connecting member which connects proximal ends of the two flexible piercing members.

4. The tissue-piercing device according to claim 3, wherein the connecting member is detachable from the proximal ends of the flexible piercing members.

* * * * *